United States Patent
Iijima et al.

(10) Patent No.: US 10,022,100 B2
(45) Date of Patent: Jul. 17, 2018

(54) MEDICAL IMAGE DIAGNOSTIC APPARATUS, MEDICAL IMAGE PROCESSING APPARATUS, MEDICAL IMAGE PROCESSING METHOD AND GANTRY MOVING POSITION DETERMINATION METHOD

(71) Applicant: Toshiba Medical Systems Corporation, Otawara-shi (JP)

(72) Inventors: Yoshiaki Iijima, Tama (JP); Masatoshi Seki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 376 days.

(21) Appl. No.: 14/804,476

(22) Filed: Jul. 21, 2015

(65) Prior Publication Data
US 2015/0320380 A1 Nov. 12, 2015

Related U.S. Application Data

(63) Continuation of application No. PCT/JP2014/051087, filed on Jan. 21, 2014.

(30) Foreign Application Priority Data

Jan. 24, 2013 (JP) .................................. 2013-011211
Feb. 12, 2013 (JP) .................................. 2013-024744

(51) Int. Cl.
*A61B 6/00* (2006.01)
*G06T 7/00* (2017.01)
(Continued)

(52) U.S. Cl.
CPC .......... *A61B 6/5211* (2013.01); *A61B 6/4441* (2013.01); *A61B 6/469* (2013.01);
(Continued)

(58) Field of Classification Search
None
See application file for complete search history.

(56) References Cited

U.S. PATENT DOCUMENTS

| 5,651,043 | A | 7/1997 | Tsuyuki et al. |
| 5,883,933 | A * | 3/1999 | Goto .................. G06T 15/00 378/4 |
| 6,508,586 | B2 | 1/2003 | Oota |
| 7,379,526 | B2 * | 5/2008 | Nishide ............... A61B 6/032 378/15 |

(Continued)

FOREIGN PATENT DOCUMENTS

| JP | 7-255715 | 10/1995 |
| JP | 8-257149 | 10/1996 |

(Continued)

OTHER PUBLICATIONS

International Search Report for International Application No. PCT/JP2014/051087; dated Apr. 28, 2014 (with English translation).

(Continued)

*Primary Examiner* — Hoon Song
(74) *Attorney, Agent, or Firm* — Oblon, McClelland, Maier & Neustadt, L.L.P.

(57) ABSTRACT

According to one embodiment, a medical image diagnostic apparatus includes an X-ray tube, an X-ray detector, storage circuitry, slice image generation circuitry, a display. The X-ray tube generates X-rays from a predetermined focus. The X-ray detector detects X-rays which have been generated by the X-ray tube and passed through an object placed on a top plate. The storage circuitry stores volume data about the object. The slice image generation circuitry generates slice images corresponding to planes each including the focus based on the volume data and a relative position of the focus with respect to the top plate. The display displays the slice images.

18 Claims, 20 Drawing Sheets

(51) Int. Cl.
*G06T 11/00* (2006.01)
*A61B 6/03* (2006.01)

(52) U.S. Cl.
CPC ............ *A61B 6/487* (2013.01); *A61B 6/5223* (2013.01); *A61B 6/547* (2013.01); *G06T 7/0012* (2013.01); *G06T 11/003* (2013.01); *A61B 6/032* (2013.01); *A61B 6/4233* (2013.01); *A61B 6/463* (2013.01); *G06T 2207/10081* (2013.01); *G06T 2207/10116* (2013.01); *G06T 2207/30004* (2013.01); *G06T 2210/41* (2013.01); *G06T 2211/40* (2013.01)

(56) References Cited

U.S. PATENT DOCUMENTS

| | | | |
|---|---|---|---|
| 2002/0085681 A1 | 7/2002 | Jensen | |
| 2007/0064984 A1* | 3/2007 | Vassa | G06F 3/1454 |
| | | | 382/128 |
| 2012/0155605 A1* | 6/2012 | Yazaki | A61B 6/488 |
| | | | 378/8 |

FOREIGN PATENT DOCUMENTS

| | | |
|---|---|---|
| JP | 2004-517670 | 6/2004 |
| JP | 4737808 | 5/2011 |

OTHER PUBLICATIONS

Written Opinion for International Application No. PCT/JP2014/051087; dated Apr. 28, 2014.

* cited by examiner

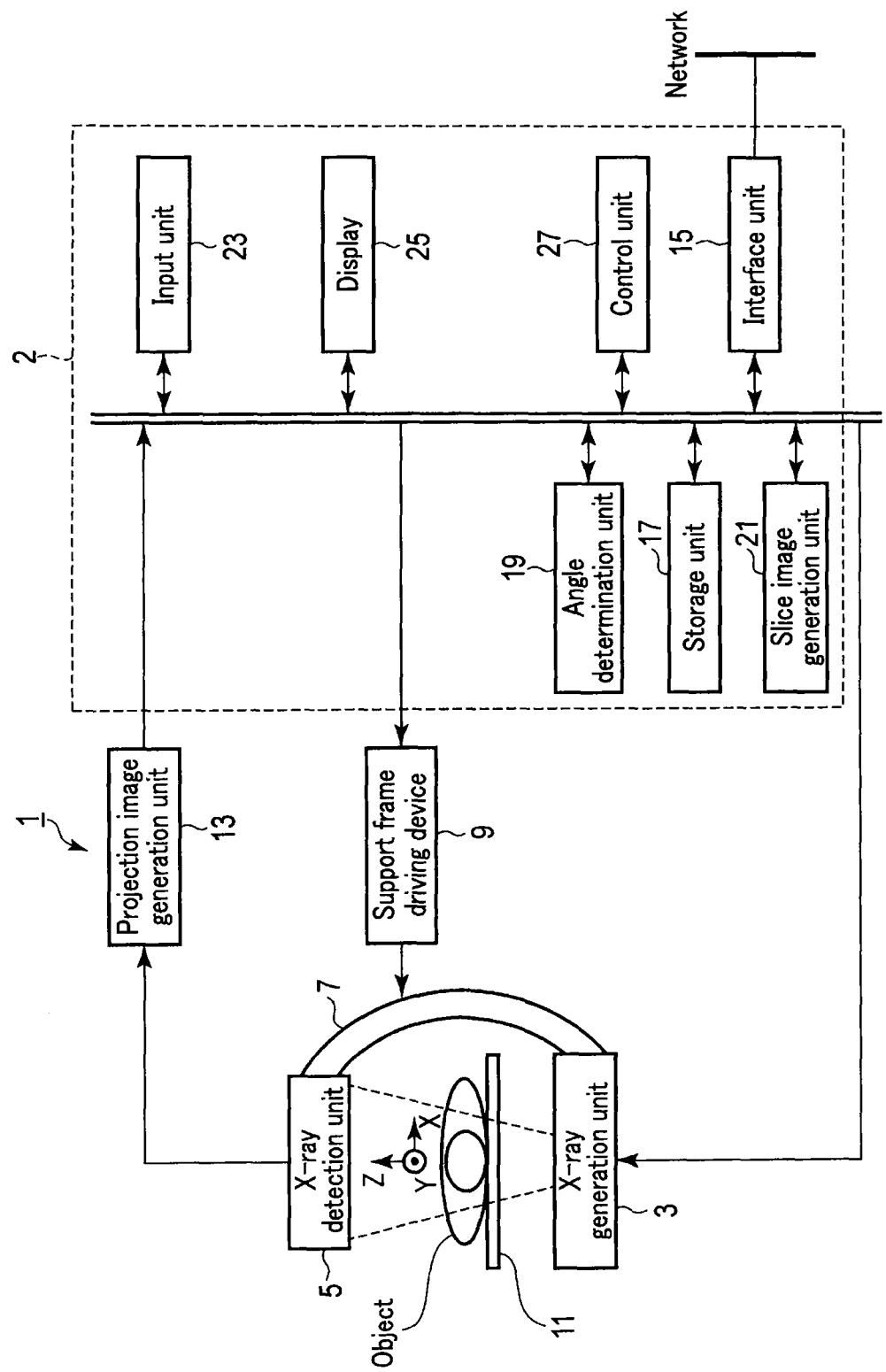
F I G. 1

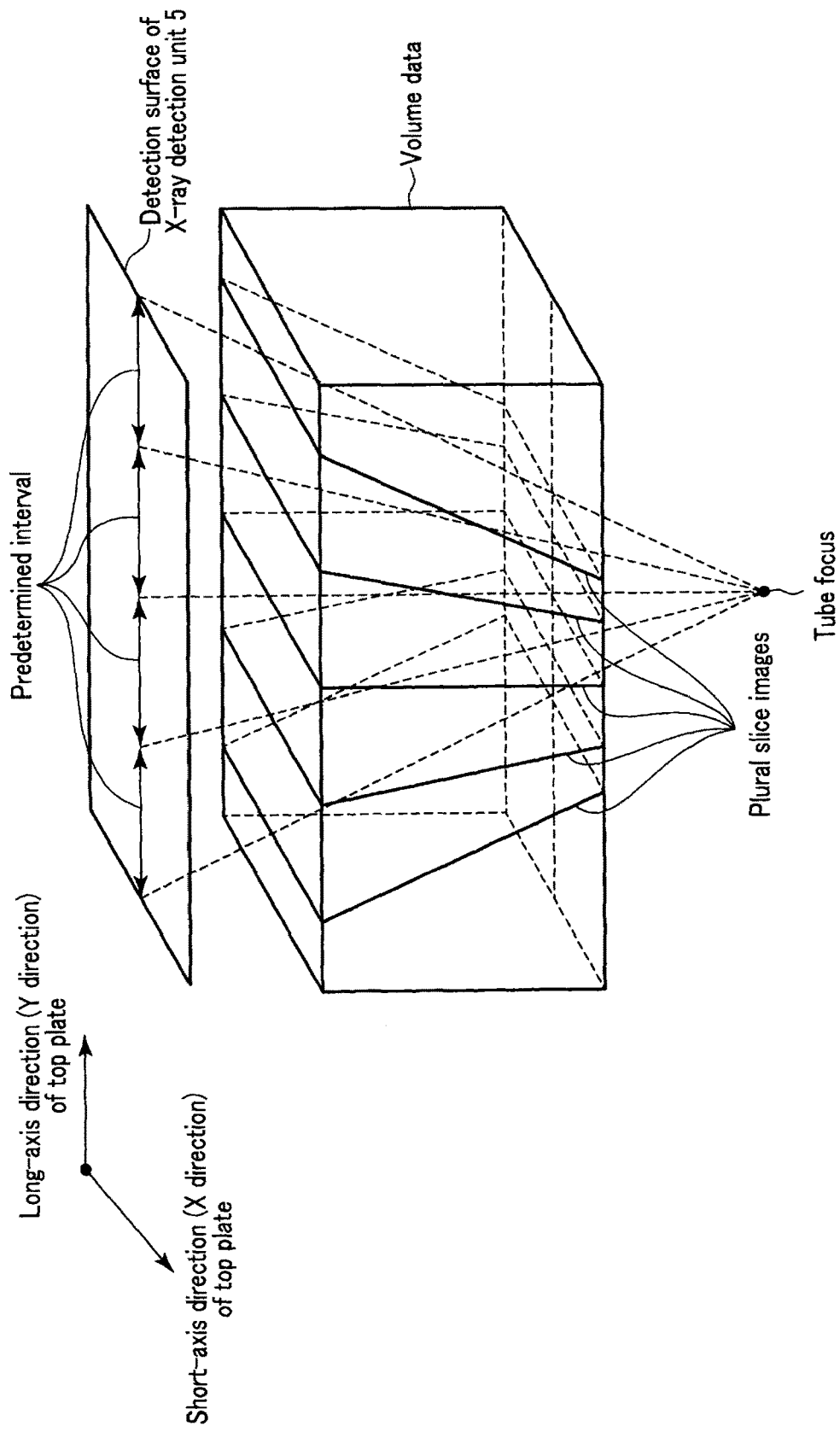
F I G. 2

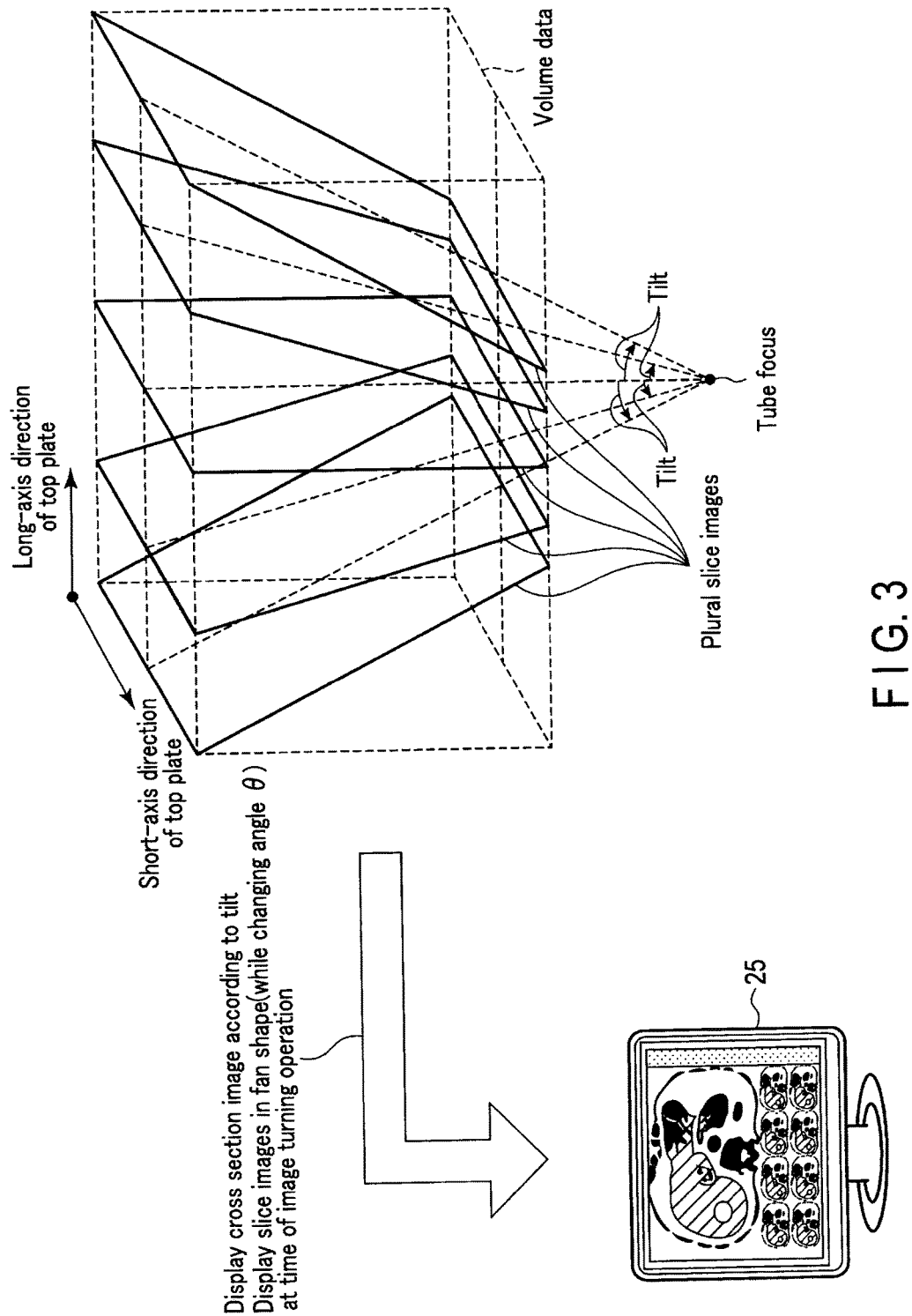
F I G. 3

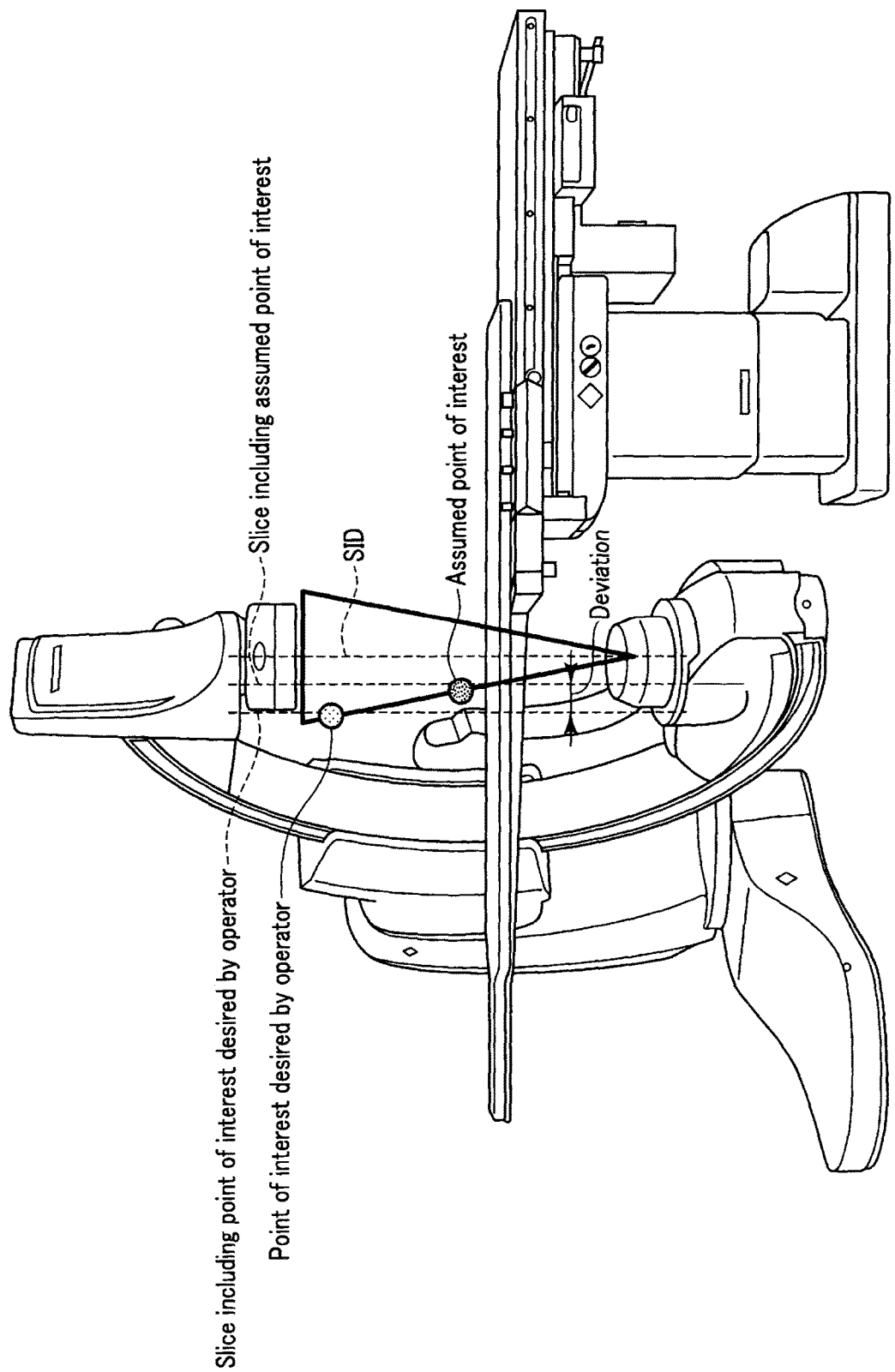
F I G. 22

MEDICAL IMAGE DIAGNOSTIC APPARATUS, MEDICAL IMAGE PROCESSING APPARATUS, MEDICAL IMAGE PROCESSING METHOD AND GANTRY MOVING POSITION DETERMINATION METHOD

CROSS-REFERENCE TO RELATED APPLICATIONS

This application is a Continuation Application of PCT Application No. PCT/JP2014/051087, filed Jan. 21, 2014 and based upon and claims the benefit of priority from the Japanese Patent Application No. 2013-011211, filed Jan. 24, 2013 and the Japanese Patent Application No. 2013-024744, filed Feb. 12, 2013, the entire contents of all of which are incorporated herein by reference.

FIELD

Embodiments described herein relate generally to a medical image diagnostic apparatus, a medical image processing apparatus, a medical image processing method and a gantry moving position determination method.

BACKGROUND

Conventionally, there is provided an IVR (interventional radiology)-CT (Computed Tomography) apparatus obtained by combining an X-ray CT apparatus and an X-ray diagnostic apparatus. The IVR-CT apparatus has, for example, a function of supporting an operation such as puncture. In this case, the IVR-CT apparatus can generate MPR (Multi-Planar Reconstruction) images including an axial image, sagittal image, coronal image based on a point designated on a generated projection image.

That is, the conventional IVR-CT apparatus can display three types of MPR images. An axial image is generated according to, for example, an axial slice calculated based on a preset temporary height and a position designated on a projection image, as shown in FIGS. 20, 21, and 22. At this time, the axial image includes a point of interest assumed based on the preset temporary height and the position designated on the projection image. However, the assumed point of interest may deviate from a point of interest desired by an operator. Consequently, the conventional IVR-CT apparatus cannot display the point of interest desired by the operator.

The IVR-CT apparatus determines a position to which a CT gantry is to be desirably moved, as follows. First, a point (to be referred to as an input point hereinafter) desired by the operator is input on the projection image. A temporary point of interest (to be referred to as an assumed point hereinafter) is determined based on the preset temporary height and the input point. The moving position of the CT gantry is determined based on the coordinate of the assumed point in the long-axis direction of a top plate (FIG. 20). In the above method, for example, as shown in FIG. 20, a position at a predetermined height from the upper surface of the top plate is set as a point desired by the operator. Therefore, as shown in FIGS. 21 and 22, when the distance (to be referred to as the height of the point of interest hereinafter) between the top plate and the position of the point of interest desired by the operator is different from the temporary height, the CT gantry moving position corresponding to the point of interest desired by the operator unwantedly deviates from that determined by the above method.

Consequently, when the position designated on the projection image deviates from a line segment which passes through the center position of an X-ray detector and is parallel to the short-axis direction of the top plate, the CT gantry moving position deviates from the position desired by the operator. That is, the determination accuracy of the CT gantry moving position degrades.

Furthermore, to accurately determine the CT gantry moving position, for example, X-ray imaging may be executed for an object a plurality of times. In this case, the radiation exposure dose of the object undesirably increases.

BRIEF DESCRIPTION OF THE DRAWINGS

FIG. 1 is a view showing an example of the arrangement of a medical image diagnostic apparatus according to the first embodiment.

FIG. 2 is a view showing an example of a plurality of generated slice images together with the detection surface of an X-ray detector, volume data, and a tube focus according to the first embodiment.

FIG. 3 is a view showing an example of display of the plurality of generated slice images according to the first embodiment.

FIG. 22 is a view showing the conventional technique.

DETAILED DESCRIPTION

Figure 4:
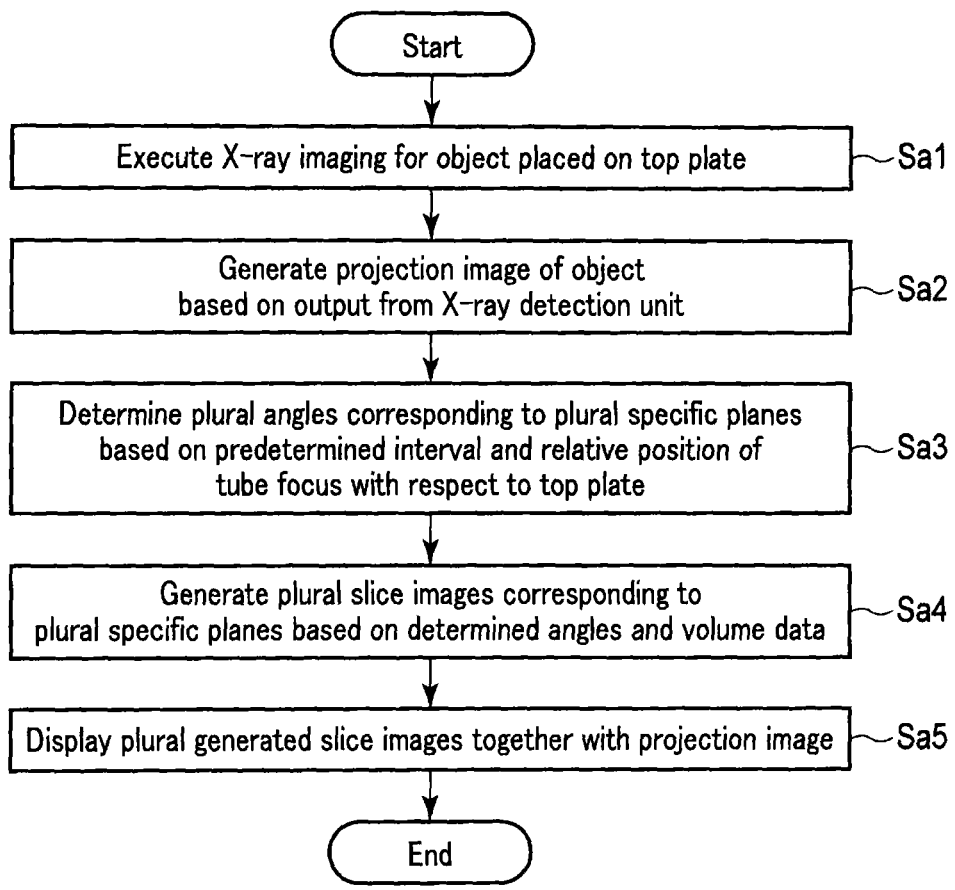
FIG. 4 is a flowchart illustrating an example of the procedure of slice image generation processing according to the first embodiment.

In general, according to one embodiment, a medical image diagnostic apparatus includes an X-ray tube, an X-ray detector, storage circuitry, slice image generation circuitry and a display.

The X-ray tube generates X-rays from a predetermined focus. The X-ray detector detects X-rays which have been generated by the X-ray tube and passed through an object placed on a top plate. The storage circuitry stores volume data about the object. The slice image generation circuitry generates a plurality of slice images corresponding to a plurality of planes each including the focus based on the volume data and a relative position of the focus with respect to the top plate. The display displays the slice images.

Medical image diagnostic apparatuses according to embodiments will be described below with reference to the accompanying drawings. In the following description, the same reference numerals denote components having almost the same functions and arrangements, and a repetitive description thereof will be made, only as needed.

First Embodiment

FIG. 1 shows the arrangement of a medical image diagnostic apparatus 1 according to the first embodiment. The medical image diagnostic apparatus 1 includes an X-ray generation unit 3, an X-ray detection unit 5, a support frame 7, a support frame driving device 9, a top plate 11, a projection image generation unit 13, an interface unit 15, storage unit 17, an angle determination unit 19, a slice image generation unit 21, input unit 23, a display 25, and control unit 27.

The X-ray generation unit 3 includes an X-ray tube and a high-voltage generator (not shown). The high-voltage generator (not shown) generates a tube current to be supplied to the X-ray tube, and a tube voltage to be applied to the X-ray tube. The high-voltage generator supplies a tube current suitable for each of X-ray imaging and X-ray fluoroscopy to the X-ray tube, and applies a tube voltage suitable for each of X-ray imaging and X-ray fluoroscopy to the X-ray tube. The X-ray tube generates X-rays from an X-ray focus (to be referred to as a tube focus hereinafter) based on the tube current supplied from the high-voltage generator and the tube voltage applied by the high-voltage generator.

The X-ray detection unit 5 detects X-rays which have been generated by the X-ray tube and passed through an object P. The X-ray detection 5 includes, for example, a flat panel detector (to be referred to as an FPD hereinafter). The FPD includes a plurality of semiconductor detection elements. The types of semiconductor detection elements include a direct conversion type and an indirect conversion type. The direct conversion type is a form of directly converting incident X-rays into an electrical signal. The indirect conversion type is a form of converting incident X-rays into light through a phosphor and converting the light into an electrical signal. The electrical signals generated by the plurality of semiconductor detection elements upon incidence of X-rays are output to an analog-to-digital converter (to be referred to as an A/D converter hereinafter) (not shown). The A/D converter converts an electrical signal into digital data. The A/D converter outputs the digital data to a preprocessing unit (not shown). Note that an image intensifier may be used as the X-ray detection unit 5. For the sake of convenience, among the plurality of semiconductor detection elements, a plurality of semiconductor detection elements parallel to the short-axis direction of the top plate will be referred to as a short-axis direction parallel element group hereinafter. The FPD includes a plurality of short-axis direction parallel element groups in the long-axis direction of the top plate.

The support frame 7 movably supports the X-ray generation unit 3 and the X-ray detection unit 5. More specifically, the support frame 7 includes, for example, a C-arm and C-arm support portion (neither of which is shown). The X-ray generation unit 3 and the X-ray detection unit 5 are mounted on the C-arm so as to face each other. Note that an Ω-arm may be used instead of the C-arm. The C-arm support portion slidably supports the C-arm in a direction (to be referred to as the first direction hereinafter) along the C shape of the C-arm. In addition, the C-arm support portion rotatably supports the C-arm about the connection portion of the C-arm and the C-arm support portion in a direction (to be referred to as the second direction hereinafter) perpendicular to the first direction. Note that the C-arm support portion can also support the C-arm to be translatable in the short-axis direction (the X direction in FIGS. 1 and 2) and long-axis direction (the Y direction in FIGS. 1 and 2) of the top plate 11 (to be described later). In addition, the C-arm supports the X-ray generation unit 3 and the X-ray detection unit 5 so as to change the distance (to be referred to as an SID (Source Image Distance) hereinafter) between the X-ray generation unit 3 and the X-ray detection unit 5.

The support frame driving device 9 drives the support frame 7 under the control of the control unit 27 (to be described later). More specifically, the support frame driving device 9 supplies a driving signal corresponding to a control signal from the control unit 27 to the C-arm support portion to slide the C-arm in the first direction and rotate it in the second direction (CRA or CAU). At the time of X-ray fluoroscopy and X-ray imaging, the object P placed on the top plate 11 is arranged between the X-ray generation unit 3 and the X-ray detection unit 5. The support frame driving device 9 outputs the tilt of the detection surface (to be referred to as an X-ray detection surface hereinafter) of the X-ray detection unit 5 with respect to the top plate 11 to the angle determination unit 19 (to be described later).

A top plate driving unit (not shown) moves the top plate 11 by driving it under the control of the control unit 27 (to be described later). More specifically, the top plate driving unit slides the top plate 11 in the short-axis direction (the X direction in FIG. 1) of the top plate 11 or the long-axis direction (the Y direction in FIG. 1) of the top plate 11 based on a control signal from the control unit 27. The top plate driving unit moves the top plate 11 up and down in the vertical direction (the Z direction in FIG. 1). In addition, the top plate driving unit may rotate the top plate 11 to tilt it about at least one of the long-axis direction and short-axis direction as a rotation axis (the X- or Y-axis in FIG. 1).

The preprocessing unit (not shown) executes preprocessing for the digital data output from the X-ray detection unit 5. The preprocessing includes, for example, sensitivity non-uniformity correction between channels in the X-ray detection unit 5, and correction concerning an excessive decrease in signal level or data omission due to a strong X-ray absorber such as a metal. The projection image generation unit 13 (to be described later) processes the preprocessed digital data.

The projection image generation unit 13 generates a captured image based on the preprocessed digital data after X-ray imaging at an imaging position. The projection image generation unit 13 generates a fluoroscopic image based on the preprocessed digital data after X-ray fluoroscopy at a fluoroscopy position. Captured images and fluoroscopic images will be collectively referred to as projection images hereinafter. The projection image generation unit 13 outputs the generated projection image to the display 25 and the storage unit 17 (both of which will be described later).

The interface unit 15 is, for example, an interface for a network and an external storage device (not shown). Data such as a projection image obtained by the medical image diagnostic apparatus 1, an analysis result, and the like can be transferred to another apparatus via the interface 15 and the network. The interface unit 15 captures volume data from a medical image generation apparatus (not shown) in the object via the network. The interface unit 15 outputs the captured volume data to the storage unit 17 (to be described later). Examples of the medical image generation apparatus are an X-ray CT apparatus, magnetic resonance imaging apparatus, and X-ray diagnostic apparatus which can generate volume data.

The storage unit 17 stores various projection images generated by the projection image generation unit 13, control programs for the medical image diagnostic apparatus 1, a diagnosis protocol, an operator instruction sent from the input unit 23 (to be described later), various data groups such as imaging conditions and fluoroscopy conditions, the volume data of the object sent via the interface unit 15 and the network, a predetermined interval for slice image generation processing (to be described later), and the like. The predetermined interval is, for example, the interval between two short-axis direction parallel element groups adjacent to each other along the long-axis direction. Note that the predetermined interval may be a predetermined length along the long-axis direction. The storage unit 17 stores the SID and the relative position between the top plate 11 and the position of the tube focus with respect to the stored projection image. The storage unit 17 may store a program (to be referred to as a medical image processing program hereinafter) for slice image generation processing of generating a plurality of slice images based on the volume data by using the relative position and predetermined interval as input values. Note that the storage circuitry 17 stores various programs to be executed by processing circuitry.

Based on the relative position between the tube focus and each of the plurality of short-axis direction parallel element groups, the angle determination unit 19 determines the angle between a plane which includes a line segment associated with the SID and is parallel to the short-axis direction and a plane which includes the position of the tube focus and each of the plurality of short-axis direction parallel element groups and is parallel to the short-axis direction. That is, the angle determination unit 19 determines a plurality of angles corresponding to the plurality of short-axis direction parallel element groups. The angle determination unit 19 outputs the plurality of determined angles to the slice image generation unit 21. This specifies a plurality of planes (to be referred to as specific planes hereinafter) each of which includes the position of the tube focus and one short-axis direction parallel element group and is parallel to the short-axis direction. Note that when the X-ray detection surface is not parallel to the top plate 11, the angle determination unit 19 may determine the angle based on the above relative position and the tilt of the X-ray detection surface with respect to the top plate 11.

The slice image generation unit 21 generates a plurality of slice images corresponding to the plurality of angles based on the plurality of determined angles and the volume data. That is, the slice image generation unit 21 generates a plurality of slice images corresponding to the plurality of specific planes. FIG. 2 is a view showing examples of the plurality of generated slice images together with the X-ray detection surface, volume data, and tube focus. As shown in FIG. 2, each of the plurality of slice images is generated in a fan shape around the tube focus along the long-axis direction. The slice image generation unit 21 outputs the plurality of generated slice images to the display 25 (to be described later) in accordance with a predetermined operation via the input unit 23 (to be described later). More specifically, the slice image generation unit 21 generates a plurality of slice images by using, as a trigger, an instruction from the input unit 23 (to be described later).

Note that based on the volume data and a position (point of interest) input on the slice image via the input unit 23 (to be described later), the slice image generation unit 21 may generate a slice image (coronal image) parallel to the top plate 11, and a slice image (sagittal image) perpendicular to the coronal image and parallel to the long-axis direction. In this case, the slice image generation unit 21 outputs the generated coronal image and sagittal image to the display 25 (to be described later).

For example, when the operator inputs a point of interest via the input unit 23 on the slice image corresponding to the second plane (to be described later), the slice image generation unit 21 generates three slice images corresponding to three orthogonal slices each including the point of interest. The three slice images are an axial image, coronal image, and sagittal image each of which includes the point of interest. The generated three slice images (axial image, coronal image, and sagittal image) are displayed on the display 25.

The input unit 23 inputs imaging conditions for X-ray imaging and fluoroscopy conditions for X-ray fluoroscopy which are desired by the operator, a fluoroscopy/imaging position, the start and end of X-ray fluoroscopy, switching between display of the projection image and display of the plurality of slice images, and the like. More specifically, the input unit 23 loads various types of instructions, commands, information, selections, and settings from the operator into the medical image diagnostic apparatus 1. The fluoroscopy/imaging position is defined by, for example, an angle with respect to a reference position. For example, if the starting point in the first oblique direction (RAO), second oblique direction (LAO), cranial direction (CRA), and caudal direction (CAU) is the fluoroscopy/imaging position and the origin of the three orthogonal axes in FIG. 1 is the reference position, the fluoroscopy position angle is 0°.

The input unit 23 includes a trackball, switch buttons, mouse, keyboard, and the like (none are shown) for, for example, setting a region of interest. The input unit 23 detects the coordinates of the cursor displayed on a display screen and outputs the detected coordinates to the control unit 27 (to be described later). Note that the input unit 23 may be a touch panel provided to cover the display screen. In this case, the input circuitry 23 detects touched and instructed coordinates by a coordinate reading principle such as an electromagnetic induction scheme, magnetostriction scheme, or a pressure sensitive' scheme, and outputs the detected coordinates to the control unit 27.

The input unit 23 includes a button (to be referred to as a slice image display button hereinafter) for displaying a plurality of slice images. When the slice image display button is pressed, the input unit 23 outputs a slice image generation instruction to the slice image generation unit 21. The input unit 23 inputs an image turning instruction to turn over the plurality of generated slice images in the long-axis direction. The image turning instruction is input by, for example, rotation of a wheel provided in the mouse. Note that the input unit 23 can also input a position for generating a sagittal image and coronal image on the displayed slice image.

The display 25 displays the projection image generated by the projection image generation function 13. The display 25 displays the slice images generated by the slice image generation unit 21. The display 25 executes an image turning operation for the displayed slice images according to the rotation of the wheel. More specifically, in accordance with the rotation of the wheel, the display 25 sequentially switches and displays the plurality of slice images along the long-axis direction. FIG. 3 is a view showing an example of display of the plurality of generated slice images. As shown in FIG. 3, the display 25 displays the slice image according to the tilt. At the time of an image turning operation, the display 25 displays the slice images in a fan shape, that is, while changing the angle of the tilt θ. Note that the display 25 may display the sagittal image and coronal image generated by the slice image generation unit 21 together with the slice image.

The control unit 27 includes a CPU (Central Processing Unit) and memory (neither of which is shown). The control unit 27 temporarily stores, in the memory (not shown), information such as an operator instruction, imaging conditions, and fluoroscopy conditions sent from the input unit 23. The control unit 27 controls the X-ray generation unit 3, support frame 7, and the like to execute X-ray imaging according to the operator instruction, imaging conditions, and the like stored in the memory. The control unit 27 controls the high-voltage generator, X-ray generation unit 3, support frame 7, top plate driving unit, and the like to execute X-ray fluoroscopy according to the operator instruction, fluoroscopy conditions, and the like stored in the memory. The control unit 27 may control the slice image generation unit 21 and the like to generate a plurality of slice images by using, as a trigger, pressing of the slice image display button.

(Slice Image Generation Function)

The slice image generation function is a function of generating a plurality of slice images based on a plurality of determined angles and volume data. The processing (to be referred to as slice image generation processing hereinafter) of the slice image generation function will be described below.

FIG. 4 is a flowchart illustrating an example of the procedure of the slice image generation processing.

X-ray imaging (or fluoroscopy) is executed for the object placed on the top plate 11 (step Sa1). A projection image of the object is generated based on an output from the X-ray detection unit 5 (step Sa2). A plurality of angles corresponding to a plurality of specific planes are determined based on a predetermined interval and the relative position of the tube focus with respect to the top plate 11 (step Sa3). A plurality of slice images corresponding to the plurality of specific planes are generated based on the determined angles and the volume data (step Sa4). The plurality of slice images are displayed together with the projection image (step Sa5). Note that at least one of the plurality of slice images may be displayed together with the projection image. In this case, an image turning operation may be executed along the long-axis direction for the plurality of slice images in accordance with an image turning instruction input via the input unit 23. At this time, the image turning operation is executed, for example, in a fan shape, as shown in FIGS. 2 and 3. When a position for generating a sagittal image and coronal image is input on the slice image via the input unit 23, a sagittal image and coronal image may be generated. In this case, the display 25 may display the generated sagittal image and coronal image together with the slice image.

Modification

The difference from the above embodiment is that a slice image is generated based on a position (to be referred to as a designation position) designated on the projection image.

Figure 5:
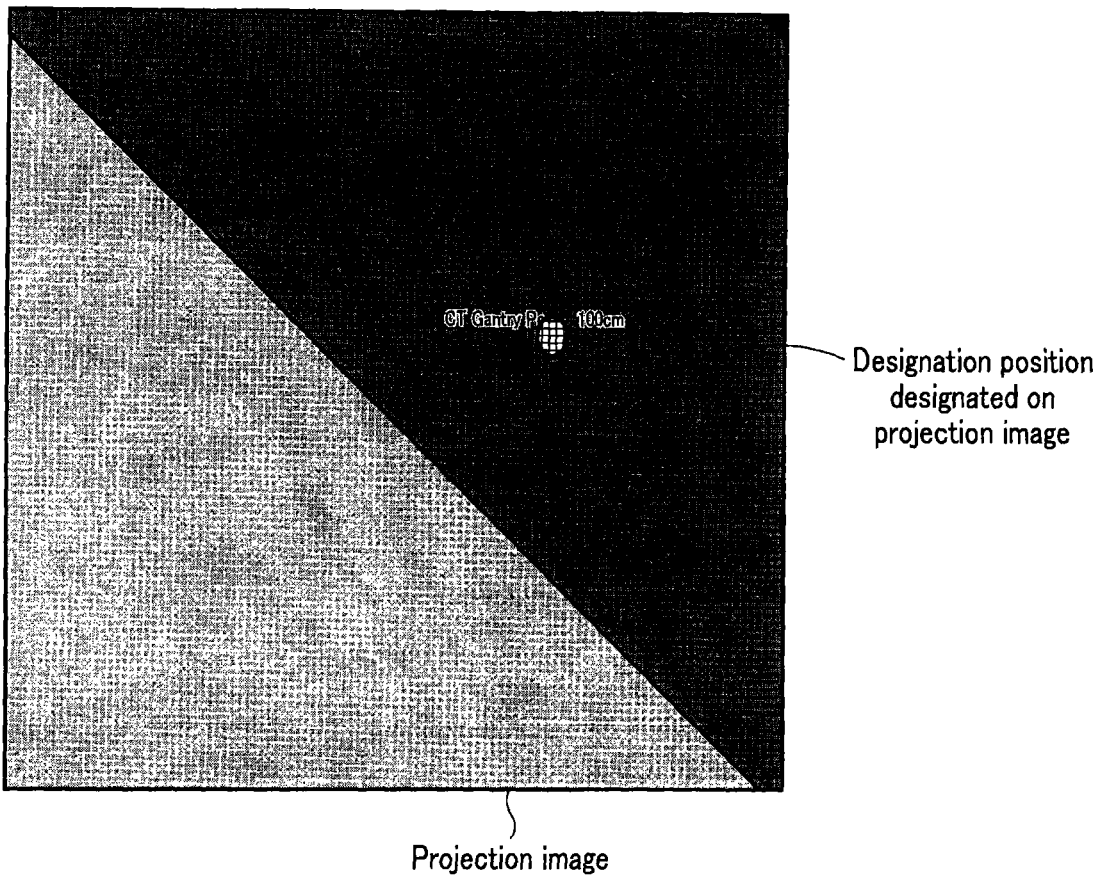
FIG. 5 is a view showing an example of a designation position designated on a projection image according to a modification of the first embodiment.

The input unit 23 inputs the designation position designated on the projection image displayed on the display 25. FIG. 5 is a view showing an example of the designation position designated on the projection image. Note that the projection image shown in FIG. 5 may be a projection image (LIH (Last Image Hold) image) obtained by executing LIH among fluoroscopic images. The projection image on which the designation position is input may be an image captured by performing X-ray imaging for the object. For the sake of descriptive convenience, assume that an image for inputting the designation position is a projection image. The input unit 23 outputs information about the designation position designated on the projection image to the angle determination unit 19. The input unit 23 can also input a position for generating a sagittal image and coronal image on the slice image generated by the slice image generation unit 21 (to be described later).

Based on the center position of the X-ray detection surface and a position (to be referred to as a specific position) on the X-ray detection surface corresponding to the designation position on the projection image, the angle determination unit 19 determines the angle between the first plane which includes the tube focus and center position and is parallel to the short-axis direction and the second plane which includes the detection surface designation position and tube focus and is parallel to the short-axis direction. More specifically, the angle determination unit 19 specifies the specific position based on the designation position. Then, the angle determination unit 19 determines the second plane based on the specific position, tube position, and center position. More particularly, the angle determination unit 19 determines the distance (to be referred to as a long-axis direction distance) between the specific position and the center position along the long-axis direction based on the coordinates of the specific position with respect to the center position as an origin. Lastly, the angle determination unit 19 determines the angle between the first and second planes based on the long-axis direction distance and SID (the distance between the tube focus and the center position).

Figure 6:
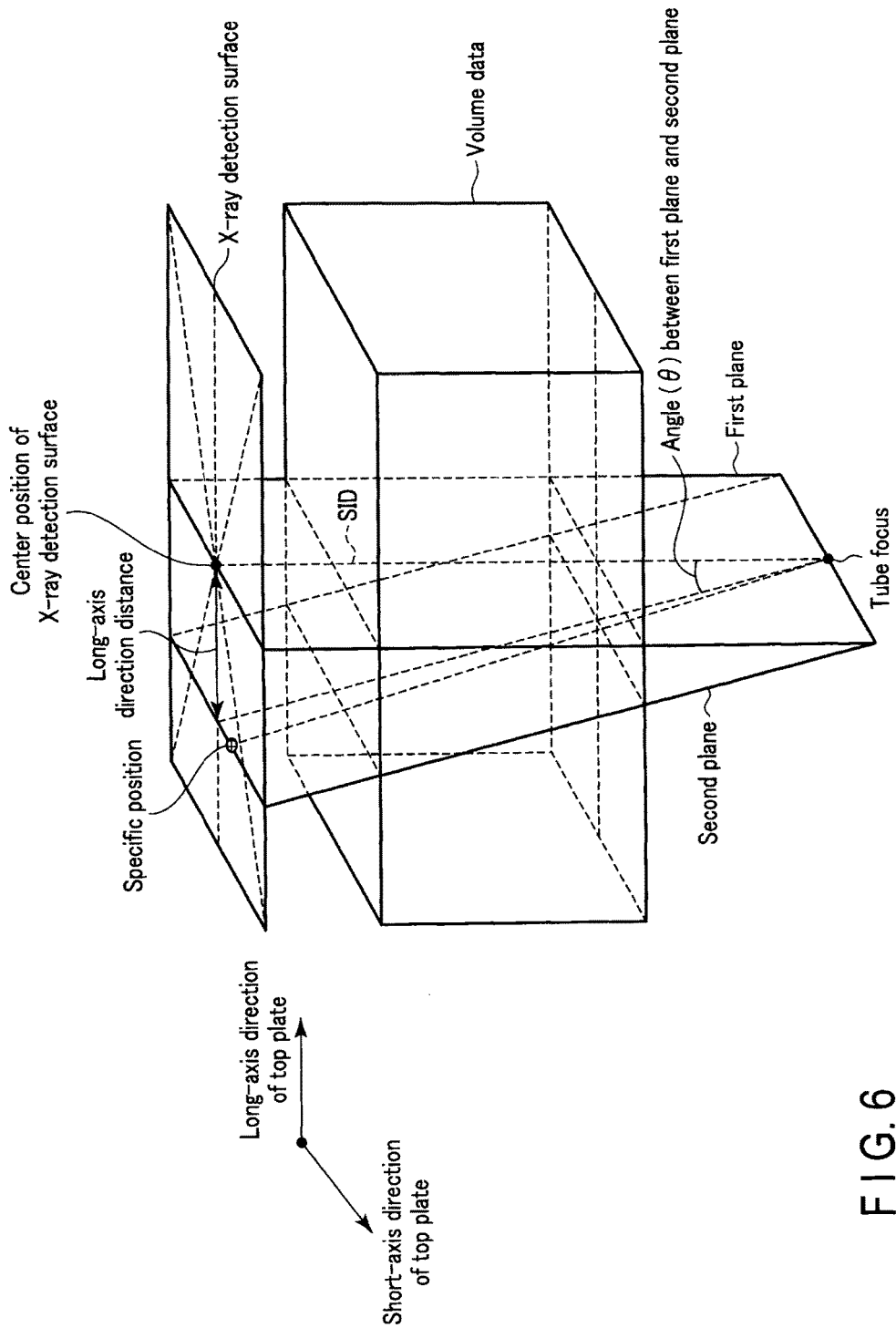
FIG. 6 is a view showing the first plane which includes the center position of the X-ray detection surface and the tube focus and is parallel to the short-axis direction of a top plate, and the second plane which includes a specific position and the tube focus and is parallel to the short-axis direction of the top plate, together with an angle θ between the first and second planes according to the modification of the first embodiment.
Figure 7:
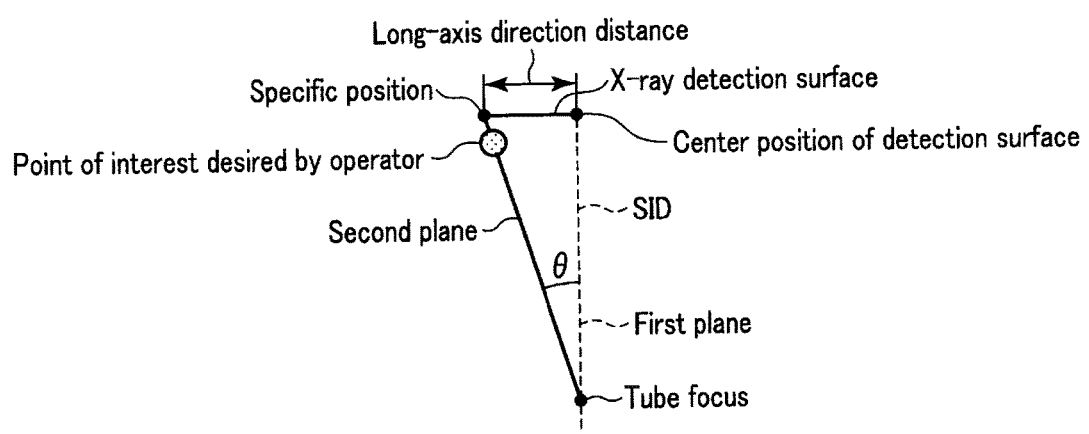
FIG. 7 is a view showing the first and second planes in FIG. 6 when viewed from the short-axis direction of the top plate according to the modification of the first embodiment.

FIG. 6 is a view showing the angle θ between the first plane which includes the tube focus and the center position of the X-ray detection surface and is parallel to the short-axis direction of the top plate and the second plane which includes the specific position and the tube focus and is parallel to the short-axis direction of the top plate. FIG. 7 is a view showing the first and second planes in FIG. 6 when viewed from the short-axis direction of the top plate 11. As shown in FIGS. 6 and 7, the angle θ is determined by calculating $\tan^{-1}$ (long-axis direction distance/SID). Note that when the X-ray detection surface is not parallel to the top plate 11, the angle determination unit 19 can execute the above processing to determine the angle by executing processing of multiplying the coordinates of the specific position by a rotation matrix according to the tilt of the X-ray detection surface with respect to the top plate 11.

Figure 8:
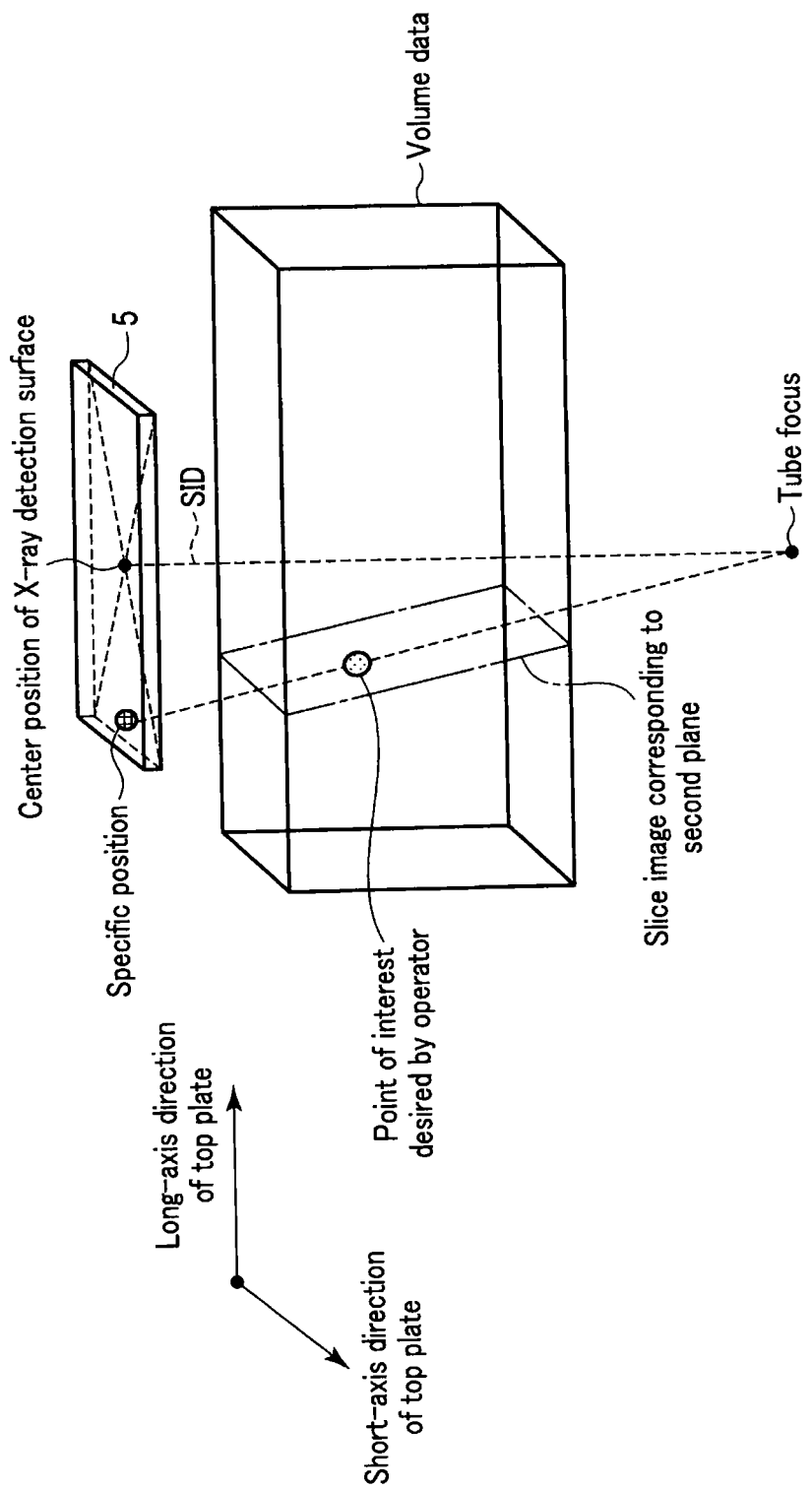
FIG. 8 is a view showing a slice image corresponding to the second plane together with the volume data, X-ray detector, tube focus, and specific position according to the modification of the first embodiment.

The slice image generation unit 21 generates a slice image corresponding to the second plane based on the volume data and angle. FIG. 8 is a view showing an example of the slice image generated by the slice image generation unit 21. As shown in FIG. 8, when the designation position is input on the projection image via the input unit 23, the specific position is specified on the X-ray detection surface. Based on the volume data and the determined angle, the slice image generation unit 21 generates a slice image corresponding to the second plane which includes a line segment connecting the specific position and tube focus.

Note that the slice image generation unit 21 may generate a coronal image and sagittal image based on the volume data and the position input on the slice image via the input unit 23. In this case, the slice image generation unit 21 outputs the generated coronal image and sagittal image to the display 25 (to be described later).

The display 25 displays the slice image generated by the slice image generation unit 21 together with the projection image on which the designation position has been input. Note that the display 25 may display the slice image generated by the slice image generation unit 21 together with the sagittal image and coronal image.

(Slice Image Generation Function)

The slice image generation function according to the modification determines the angle between the first and second planes based on the designation position designated on the projection image, the center position, and the tube focus, and generates a slice image corresponding to the second plane based on the volume data and the determined angle.

Figure 9:
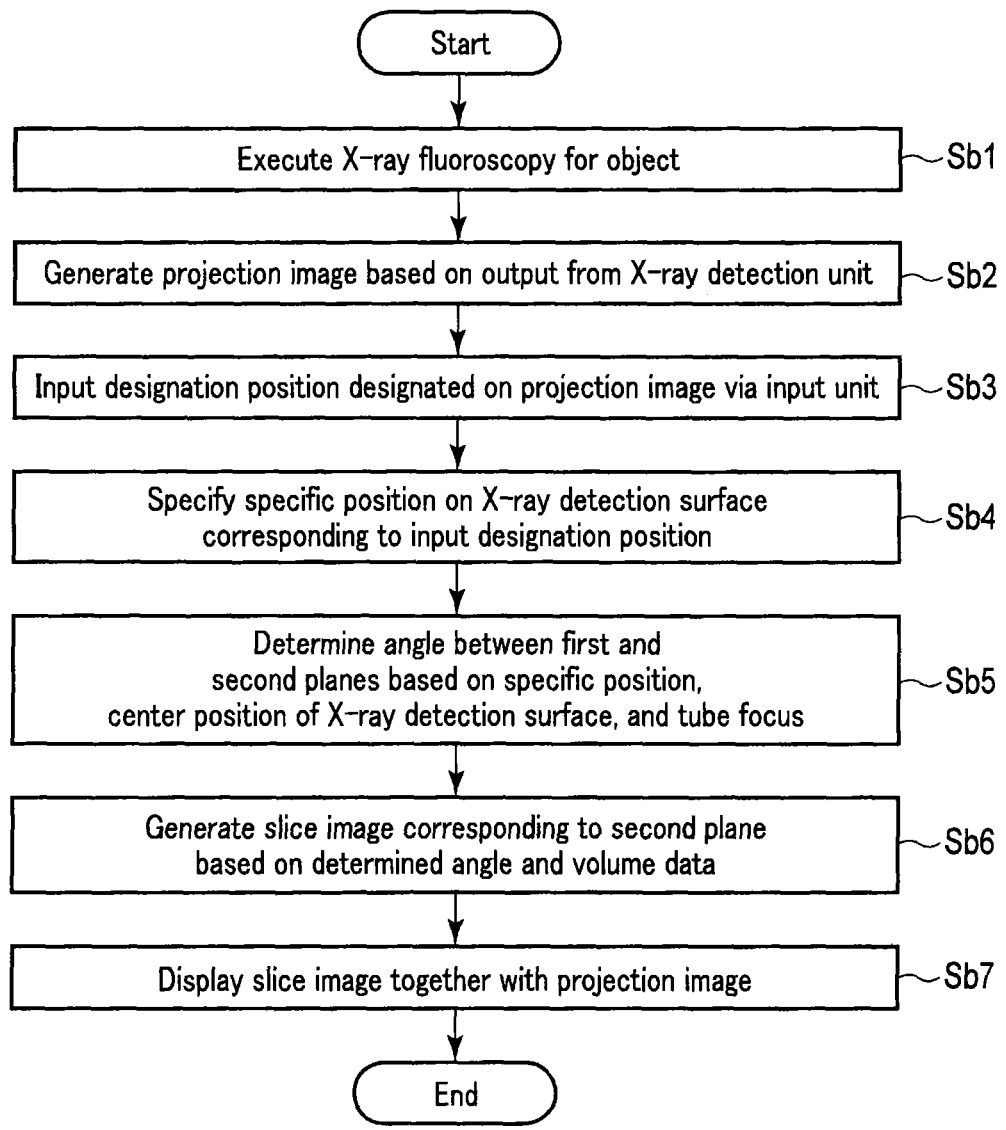
FIG. 9 is a flowchart illustrating an example of the procedure of slice image generation processing according to the modification of the first embodiment.

FIG. 9 is a flowchart illustrating an example of the procedure of slice image generation processing according to the modification.

X-ray fluoroscopy is executed for the object (step Sb1). An X-ray fluoroscopic image is displayed on the display 25. When last image hold is executed for the displayed X-ray fluoroscopic image, a projection image is generated based on an output from the X-ray detection unit 5 (step Sb2). A designation position designated on the projection image is input via the input unit 23 (step Sb3). A specific position on the X-ray detection surface corresponding to the input designation position is specified (step Sb4). The angle between the first and second planes is determined based on the specific position, center position, and tube focus (step Sb5).

A slice image corresponding to the second plane is generated based on the determined angle and the volume data (step Sb6). The generated slice image is displayed together with the projection image (step Sb7).

With the above-described arrangement, it is possible to obtain the following effects.

Based on the plurality of determined angles and the volume data, the medical image diagnostic apparatus 1 according to the first embodiment can generate a plurality of slice images corresponding to a plurality of specific planes each of which is parallel to the short-axis direction of the top plate 11 and includes the tube focus. That is, the medical image diagnostic apparatus 1 can generate a plurality of slice images coinciding with X-rays which have reached the plurality of semiconductor detection elements from the tube focus. Furthermore, the medical image diagnostic apparatus 1 can execute an image turning operation for the plurality of generated slice images in a fan shape along the long-axis direction in accordance with an operator instruction. This makes it possible to generate a slice image including a position (a portion of interest and a point of interest) desired by the operator on the projection image. Therefore, the medical image diagnostic apparatus 1 according to the first embodiment can generate a slice image including a point of interest desired by the operator.

In addition, the medical image diagnostic apparatus 1 according to the modification of the first embodiment can determine the angle between the first and second planes based on the volume data and a position designated on the projection image, and generate a slice image corresponding to the second plane based on the volume data and the determined angle. Consequently, the medical image diagnostic apparatus 1 according to the modification can generate a slice image for the designation position designated on the projection image.

As described above, the medical image diagnostic apparatus 1 can generate a slice image including a portion of interest about a point of interest desired by the operator on the projection image.

Note that in the modification of the first embodiment, when the technical concept of the medical image diagnostic apparatus 1 is implemented by a medical image processing apparatus, for example, the components surrounded by dotted lines 2 in the view shown in FIG. 1 are included. The respective processes of the slice image generation function according to the first embodiment are, for example, the processes in steps Sa3 to Sa5 in FIG. 4. In addition, the respective processes of the slice image generation function according to the modification of the first embodiment are, for example, the processes in steps Sb3 to Sb7 in FIG. 9.

The function according to the first embodiment can be implemented by installing a program for executing slice image generation processing in a computer such as a work station, and loading it onto a memory. In this case, it is possible to store the program capable of causing the computer to execute the method in a storage medium such as a magnetic disk (Floppy® disk, hard disk, or the like), an optical disk (CD-ROM, DVD, or the like), or a semiconductor memory, and distribute it.

Second Embodiment

Figure 10:
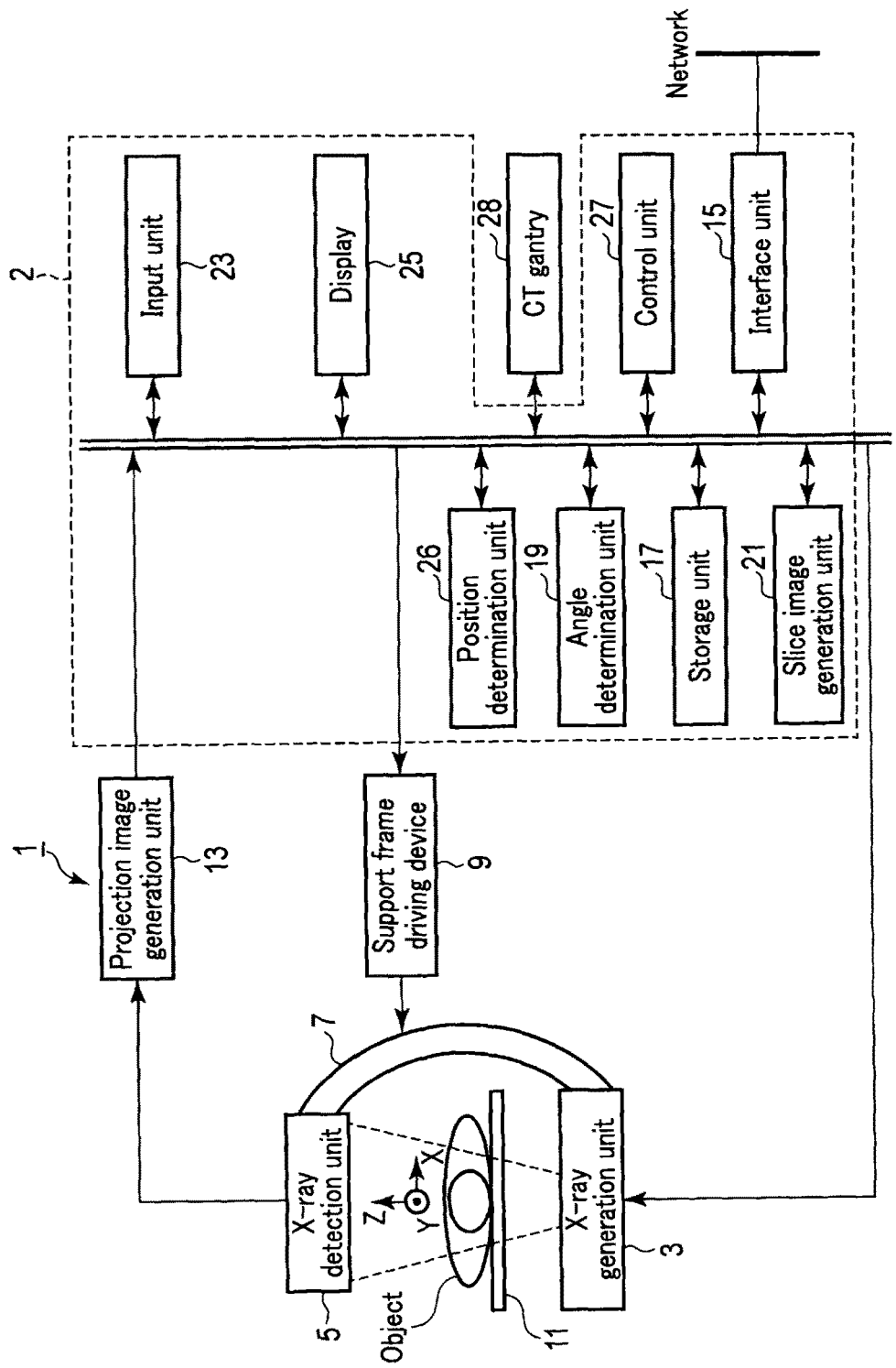
FIG. 10 is a view showing an example of the arrangement of a medical image diagnostic apparatus according to the second embodiment.

FIG. 10 shows the arrangement of a medical image diagnostic apparatus 1 according to the second embodiment. The medical image diagnostic apparatus 1 includes an X-ray generation unit 3, an X-ray detection unit 5, a support frame 7, a support frame driving device 9, a top plate 11, projection image generation unit 13, an interface unit 15, storage unit 17, an angle determination unit 19, a slice image generation unit 21, an input unit 23, a display 25, position determination unit 26, an X-ray CT (Computed Tomography) gantry (to be referred to as a CT gantry hereinafter) 28, and control unit 27.

The X-ray generation unit 3 includes the X-ray tube and a high-voltage generator (not shown). The high-voltage generator generates a tube current to be supplied to the X-ray tube, and a tube voltage to be applied to the X-ray tube. The high-voltage generator supplies a tube current suitable for each of X-ray imaging and X-ray fluoroscopy to the X-ray tube, and applies a tube voltage suitable for each of X-ray imaging and X-ray fluoroscopy to the X-ray tube. The X-ray tube generates X-rays from an X-ray focus (to be referred to as a tube focus hereinafter) based on the tube current supplied from the high-voltage generator and the tube voltage applied by the high-voltage generator.

The X-ray detection unit 5 detects the X-rays which have been generated by the X-ray generation unit 3 and passed through an object P. The X-ray detection unit 5 includes, for example, a flat panel detector (to be referred to as an FPD hereinafter). The FPD includes a plurality of semiconductor detection elements. The types of semiconductor detection elements include a direct conversion type and an indirect conversion type. The direct conversion type is a form of directly converting incident X-rays into an electrical signal. The indirect conversion type is a form of converting incident X-rays into light through a phosphor and converting the light into an electrical signal. The electrical signals generated by the plurality of semiconductor detection elements upon incidence of X-rays are output to an analog-to-digital converter (to be referred to as an A/D converter hereinafter) (not shown). The A/D converter converts an electrical signal into digital data. The A/D converter outputs the digital data to the preprocessing unit (not shown) 12. Note that an image intensifier may be used as the X-ray detection unit 5.

The support frame 7 movably supports the X-ray generation unit 3 and the X-ray detection unit 5. More specifically, the support frame 7 includes, for example, a C-arm and C-arm support portion (neither of which is shown). The X-ray generation unit 3 and the X-ray detection unit 5 are mounted on the C-arm so as to face each other. Note that an Ω-arm may be used instead of the C-arm. The C-arm support portion slidably supports the C-arm in a direction (to be referred to as the first direction hereinafter) along the C shape of the C-arm. In addition, the C-arm support portion rotatably supports the C-arm about the connection portion of the C-arm and the C-arm support portion in a direction (to be referred to as the second direction hereinafter) perpendicular to the first direction. Note that the C-arm support portion can also support the C-arm to be translatable in the short-axis direction (the X direction in FIG. 10) and long-axis direction (the Y direction in FIG. 10) of the top plate 11 (to be described later). In addition, the C-arm supports the X-ray generation unit 3 and the X-ray detection unit 5 so as to change the distance (to be referred to as an SID (Source Image Distance) hereinafter) between the X-ray generation unit 3 and the X-ray detection unit 5.

The support frame driving device 9 drives the support frame 7 under the control of the control unit 27 (to be described later). More specifically, the support frame driving device 9 supplies a driving signal corresponding to a control signal from the control unit 27 to the C-arm support portion to slide the C-arm in the first direction and rotate it in the second direction (the cranial direction (CRA) or caudal direction (CAU)). At the time of X-ray fluoroscopy and X-ray imaging, the object P placed on the top plate 11 is arranged between the X-ray generation unit 3 and the X-ray detection unit 5. The support frame driving device 9 outputs the tilt of the detection surface (to be referred to as an X-ray detection surface hereinafter) of the X-ray detection unit 5 with respect to the top plate 11 to the angle determination unit 19 (to be described later).

A top plate driving unit (not shown) moves the top plate 11 by driving it under the control of the control unit 27 (to be described later). More specifically, the top plate driving unit slides the top plate 11 in the short-axis direction (the X direction in FIG. 10) of the top plate 11 or the long-axis direction (the Y direction in FIG. 10) of the top plate 11 based on a control signal from the control unit 27. The top plate driving unit moves the top plate 11 up and down in the vertical direction (the Z direction in FIG. 10). In addition, the top plate driving unit may rotate the top plate 11 to tilt it about at least one of the long-axis direction and the short-axis direction as a rotation axis (the X- or Y-axis in FIG. 10).

The preprocessing unit (not shown) executes preprocessing for the digital data output from the X-ray detection unit 5. The preprocessing includes, for example, sensitivity nonuniformity correction between channels in the X-ray detection unit 5, and correction concerning an excessive decrease in signal level or data omission due to a strong X-ray absorber such as a metal. The preprocessing unit outputs the preprocessed digital data to the projection image generation unit 13 (to be described later).

The preprocessing unit performs preprocessing for pure raw data output from a DAS (Data Acquisition System) in the CT gantry 28 (to be described later). The preprocessing includes, for example, sensitivity nonuniformity correction processing between channels, and processing of correcting an excessive decrease in signal strength or signal omission due to a strong X-ray absorber, mainly due to a metal portion. Upon data collection, data (called raw data or projection data, projection data in this example) immediately before reconstruction processing, which is output from the preprocessing function, is stored in the storage unit 17 (to be described later) including a magnetic disk, magnetooptical disk, or semiconductor memory in association with data representing a view angle.

The projection image generation unit 13 generates a captured image based on the preprocessed digital data after X-ray imaging at an imaging position. The projection image generation unit 13 generates a fluoroscopic image based on the preprocessed digital data after X-ray fluoroscopy at a fluoroscopy position. Captured images and fluoroscopic images will be collectively referred to as projection images hereinafter. The projection image generation unit 13 outputs the generated projection image to the display 25 and the storage unit 17 (both of which will be described later).

The interface unit 15 is, for example, an interface for a network and an external storage device (not shown). Data such as a projection image obtained by the medical image diagnostic apparatus 1, an analysis result, and the like can be transferred to another apparatus via the interface unit 15 and the network. The interface unit 15 captures volume data from the CT gantry 28 (to be described later) or a medical image generation apparatus (not shown) in the object via the network. The interface unit 15 outputs the captured volume data to the storage unit 17 (to be described later). Examples of the medical image generation apparatus are a magnetic resonance imaging apparatus and X-ray diagnostic apparatus which can generate volume data.

The storage unit 17 stores various projection images generated by the projection image generation unit 13, control programs for the medical image diagnostic apparatus 1, a diagnosis protocol, an operator instruction sent from the input unit 23 (to be described later), various data groups such as imaging conditions and fluoroscopy conditions, the volume data of the object sent via the interface unit 15 and the network, and the like. The storage unit 17 stores the SID and the relative position between the top plate 11 and the position of the tube focus with respect to the stored projection image. The storage unit 17 may store a program (to be referred to as a gantry moving position determination program hereinafter) for gantry moving position determination processing (to be described later).

Based on the center position of the X-ray detection surface and a position (to be referred to as a detection surface position hereinafter) on the X-ray detection surface corresponding to the first designation position designated on the projection image via the input unit 23 (to be described later), the angle determination unit 19 determines the angle between the first plane which includes the tube focus and the center position and is parallel to the short-axis direction and the second plane which includes the first designation position and the tube focus and is parallel to the short-axis direction. More specifically, the angle determination unit 19 specifies the detection surface position based on the first designation position. Then, the angle determination unit 19 determines the second plane based on the detection surface position, tube position, and center position. More particularly, the angle determination unit 19 determines the distance (to be referred to as a long-axis direction distance hereinafter) between the detection surface position and the center position along the long-axis direction based on the coordinates of the detection surface position with respect to the center position as an origin. Lastly, the angle determination unit 19 determines the angle between the first and second planes based on the long-axis direction distance and SID.

Note that when the X-ray detection surface is not parallel to the top plate 11, the angle determination unit 19 executes the above processing to determine the angle by executing processing of multiplying the coordinates of the detection surface position by a rotation matrix according to the tilt of the X-ray detection surface with respect to the top plate 11.

Figure 11:
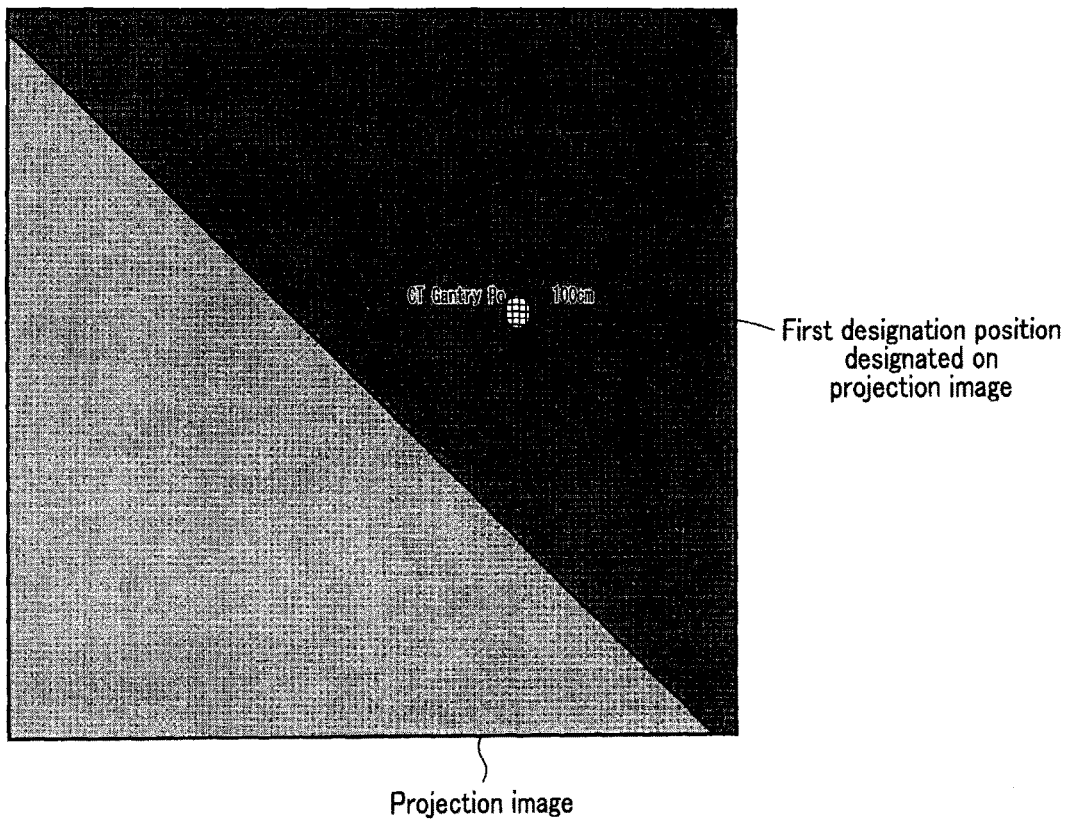
FIG. 11 is a view showing an example of a designation position designated on a projection image according to the second embodiment.

FIG. 11 is a view showing an example of the first designation position designated on the projection image. Note that the projection image shown in FIG. 11 may be a projection image (to be referred to as an LIH (Last Image Hold) image hereinafter) obtained by executing LIH among fluoroscopic images. For the sake of descriptive convenience, assume that an image for the input of the first designation position is a projection image.

Figure 12:
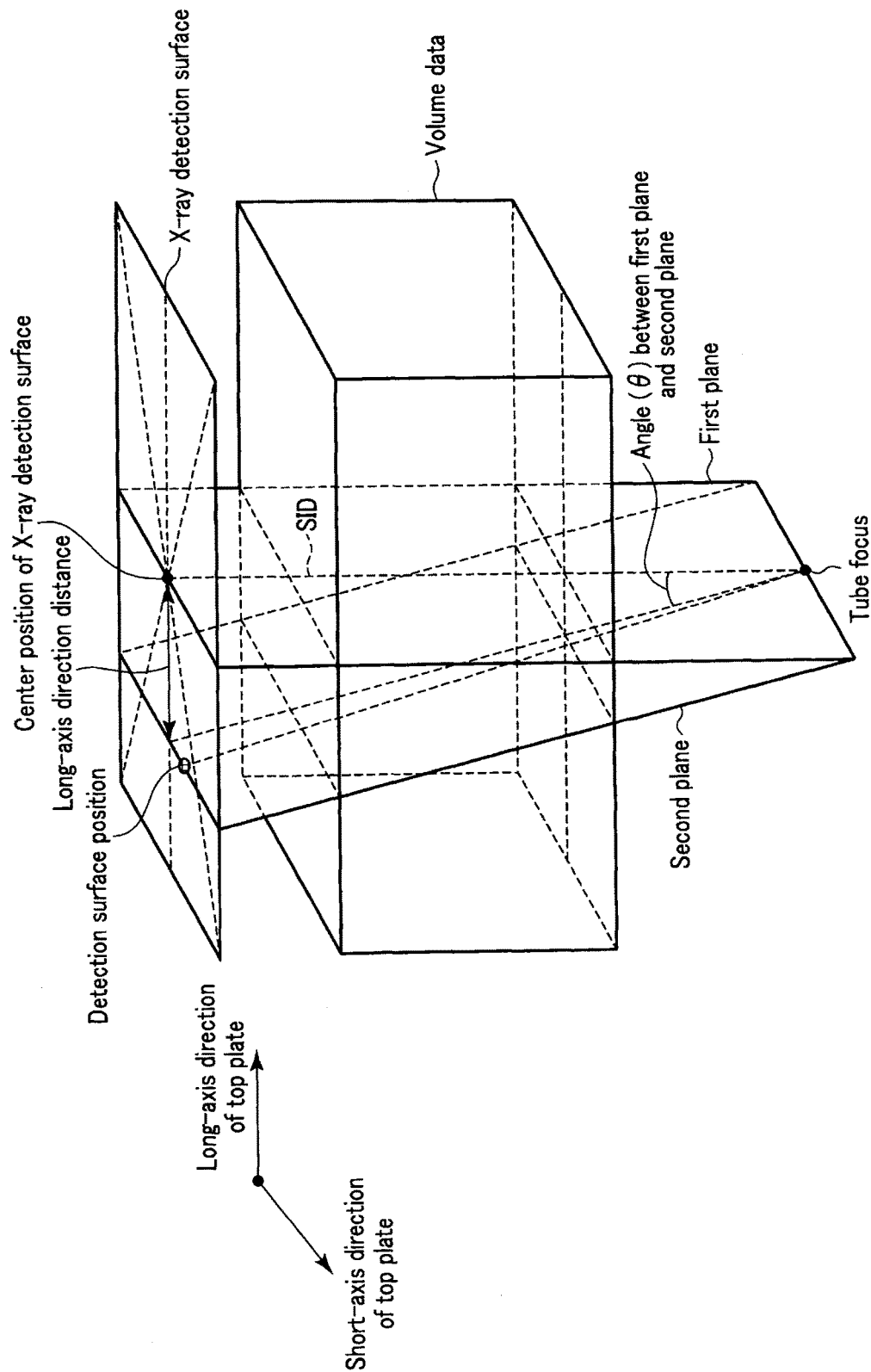
FIG. 12 is a view showing the first plane which includes the center position of an X-ray detection surface and a tube focus and is parallel to the short-axis direction of a top plate, and the second plane which includes a detection surface position and the tube focus and is parallel to the short-axis direction of the top plate, together with an angle θ between the first and second planes according to the second embodiment.
Figure 13:
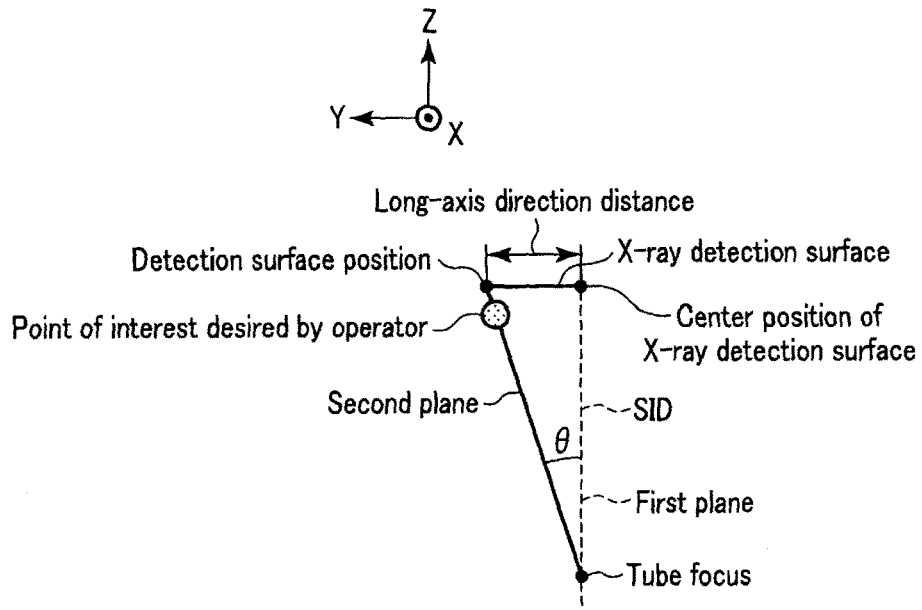
FIG. 13 is a view showing the first and second planes in FIG. 12 when viewed from the short-axis direction of the top plate according to the second embodiment.

FIG. 12 is a view showing an angle θ between the first plane which includes the center position of the X-ray detection surface and the tube focus and is parallel to the short-axis direction of the top plate and the second plane which includes the detection surface position and the tube focus and is parallel to the short-axis direction of the top plate. FIG. 13 is a view showing the first and second planes in FIG. 12 when viewed from the short-axis direction of the top plate 11. As shown in FIGS. 12 and 13, the angle θ is determined by calculating $\tan^{-1}$ (long-axis direction distance/SID).

Figure 14:
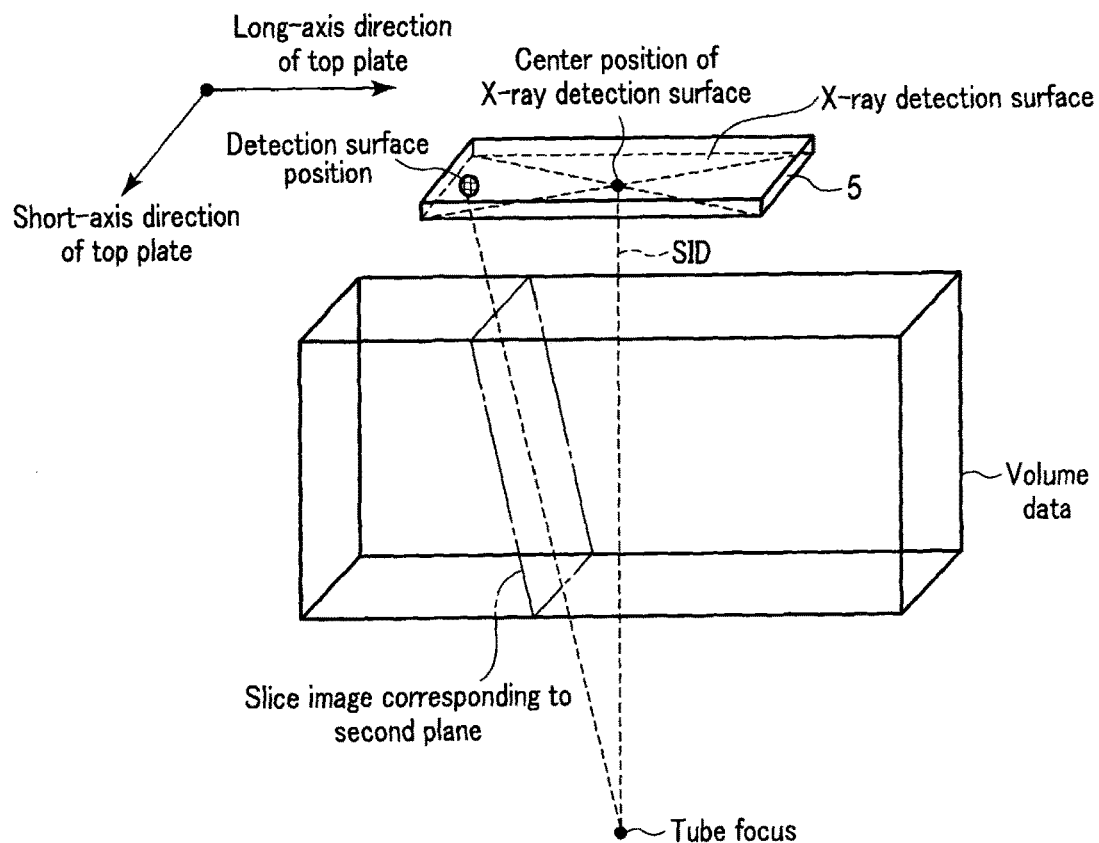
FIG. 14 is a view showing a slice image corresponding to the second plane together with volume data, an X-ray detector, the tube focus, and the detection surface position according to the second embodiment.

The slice image generation unit 21 generates a slice image corresponding to the second plane based on the volume data and angle. FIG. 14 is a view showing an example of the slice image generated by the slice image generation unit 21. As shown in FIG. 14, when a designation position is input on the projection image via the input circuitry 23, a detection surface position is specified on the X-ray detection surface. Based on the volume data and the determined angle, the slice image generation unit 21 generates a slice image corresponding to the second plane which includes a line segment connecting the detection surface position and tube focus. More specifically, the slice image generation unit 21 generates a slice image corresponding to the second plane by using, as a trigger, the input of the first designation position via the input unit 23 (to be described later).

Note that based on the volume data and the position (point of interest) input on the slice image via the input unit 23 (to be described later), the slice image generation unit 21 may generate a slice image (coronal image) parallel to the top plate 11 and a slice image (sagittal image) perpendicular to the coronal image and parallel to the long-axis direction. In this case, the slice image generation unit 21 outputs the generated coronal image and sagittal image to the display 25 (to be described later).

For example, when the operator inputs a point of interest via the input unit 23 on the slice image corresponding to the second plane, the slice image generation unit 21 generates three slice images corresponding to three orthogonal slices each including the point of interest. The three slice images are an axial image, coronal image, and sagittal image each of which includes the point of interest. The generated three slice images (axial image, coronal image, and sagittal image) are displayed on the display 25.

The display 25 displays the projection image generated by the projection image generation unit 13. The display 25 displays the slice image generated by the slice image generation unit 21. Note that the display 25 may display the sagittal image and coronal image generated by the slice image generation unit 21 together with the slice image. Also, the display 25 may display the slice image generated by the slice image generation unit 21 together with the projection image on which the designation position has been input. Note that the display 25 may display the slice image generated by the slice image generation unit 21 together with the sagittal image and coronal image.

The input unit 23 inputs imaging conditions for X-ray imaging and fluoroscopy conditions for X-ray fluoroscopy which are desired by the operator, a fluoroscopy/imaging position, the start and end of X-ray fluoroscopy, switching between display of the projection image and display of the plurality of slice images, and the like. More specifically, the input unit 23 loads various types of instructions, commands, information, selections, and settings from the operator into the medical image diagnostic apparatus 1. The fluoroscopy/imaging position is defined by, for example, an angle with respect to a reference position. For example, if the starting point in the first oblique direction (RAO), second oblique direction (LAO), cranial direction (CRA), and caudal direction (CAU) is the fluoroscopy/imaging position and the origin of the three orthogonal axes in FIG. 10 is the reference position, the fluoroscopy position angle is 0°.

The input unit 23 is implemented by a trackball, switch buttons, mouse, keyboard, and the like (none are shown) for, for example, setting a region of interest. The input unit 23 detects the coordinates of the cursor displayed on a display screen and outputs the detected coordinates to the control unit 27 (to be described later). Note that the input unit 23 may be a touch panel provided to cover the display screen. In this case, the input unit 23 detects touched and instructed coordinates by a coordinate reading principle such as an electromagnetic induction scheme, magnetostriction scheme, or a pressure sensitive scheme, and outputs the detected coordinates to the control unit 27.

Figure 15:
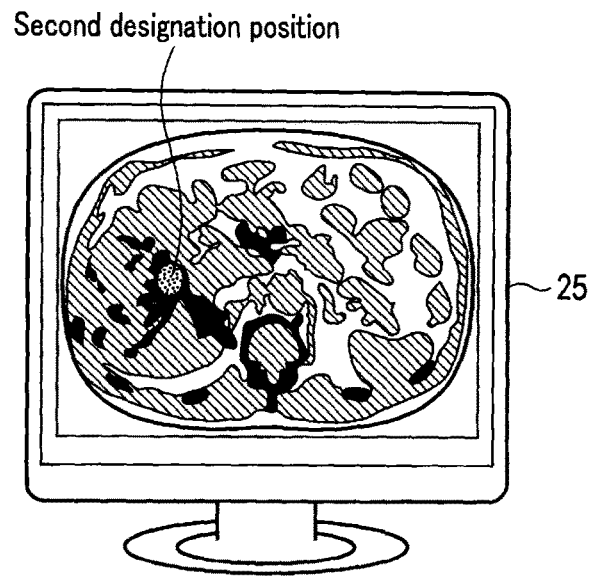
FIG. 15 is a view showing a display example of a slice image on which the second designation position has been designated according to the second embodiment.

The input unit 23 inputs the first designation position on the projection image displayed on the display 25. The input unit 23 inputs the second designation position on the slice image displayed on the display 25. FIG. 15 is a view showing a display example of the slice image on which the second designation position has been designated. The input unit 23 outputs information about the designation position designated on the projection image to the angle determination unit 19. Note that the projection image on which the designation position is input may be an image captured by performing X-ray imaging for the object. The input unit 23 can also input a position for generating a sagittal image and coronal image on the slice image generated by the slice image generation unit 21 (to be described later).

Figure 16:
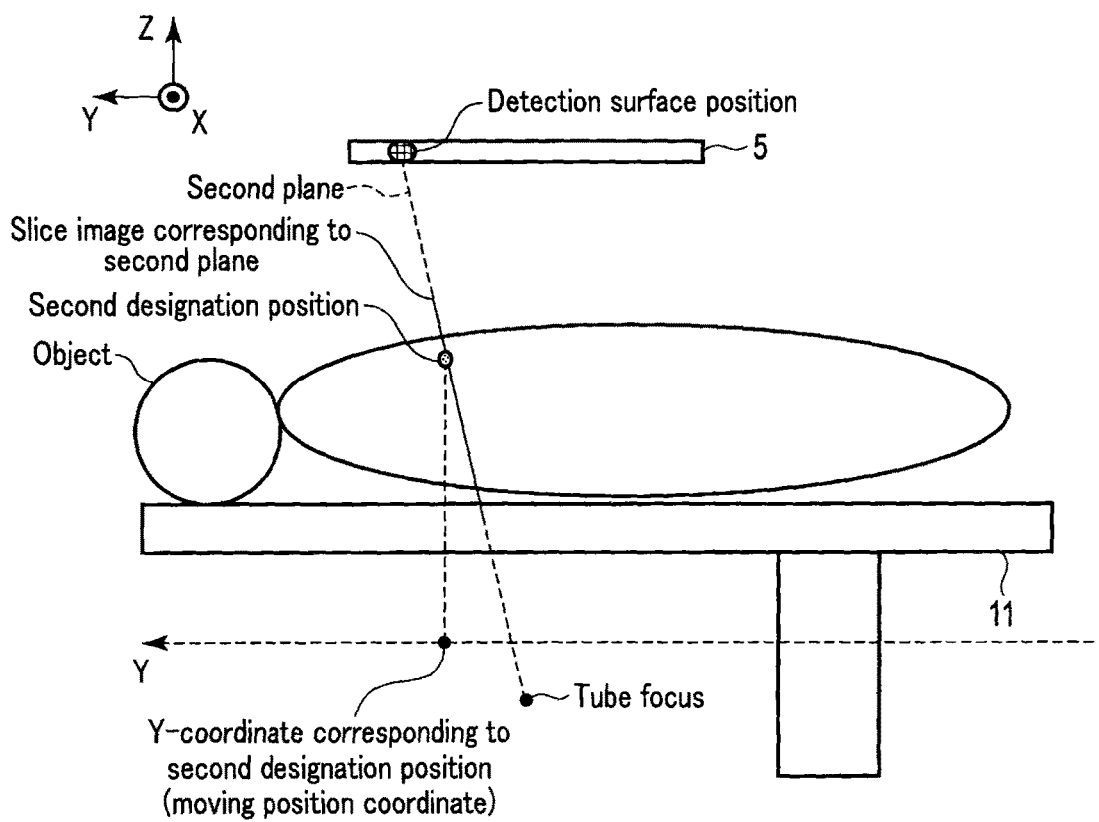
FIG. 16 is a view for explaining an example of a moving position according to the second embodiment.

Based on the second designation position designated on the slice image, the position determination unit 26 determines a moving position to which the CT gantry 28 is to be moved. More specifically, the position determination unit 26 specifies the coordinate (to be referred to as a moving position coordinate hereinafter) of the second designation position along the Y-axis (long-axis direction). The position determination unit 26 determines the moving position coordinate as a moving position. The position determination unit 26 outputs the moving position coordinate to the CT gantry 28 (to be described later). FIG. 16 is a view for explaining an example of the moving position. As shown in FIG. 16, the moving position coordinate is determined based on the second designation position. The CT gantry 28 (to be described later) is moved to the moving position coordinate.

The CT gantry 28 has a rotation support mechanism and a long-axis direction moving mechanism. The rotation support mechanism includes a rotation frame, a main frame for rotatably supporting the rotation frame about the rotation axis, and a rotation driving unit for driving rotation of the rotation frame. A high-voltage generator, an X-ray tube, an X-ray detector which is also called a two-dimensional array type or multi-array type detector, and data collection circuitry are mounted on the rotation frame. The rotation driving unit rotates the rotation frame by a direct drive or belt drive under the control of the control unit 27.

The high-voltage generator generates a high voltage to be supplied to the X-ray tube. More specifically, the high-voltage generator generates a high voltage according to a control signal input from the control unit 27 via a slip ring. Upon receiving a voltage applied from the high-voltage generator and a current supplied from the high-voltage generator, the X-ray tube emits X-rays from the X-ray focus. The X-rays emitted from the X-ray focus are shaped in, for example, a cone beam shape (pyramidal shape) by a collimator attached to the X-ray emission window of the X-ray tube. The X-ray detector is attached to the rotation frame at an angle and position facing the X-ray tube via the rotation axis. Data acquisition system (to be referred to as a DAS hereinafter) is connected to the output side of the X-ray detector. Data (pure raw data) output from the DAS is transmitted to preprocessing unit via a noncontact data transmitter using magnetic transmission/reception or optical transmission/reception. The long-axis direction moving mechanism moves the CT gantry 28 to the moving position determined by the position determination unit 26. Moving the CT gantry 28 to the moving position arranges the object placed on the top plate 11 within an imaging region having a cylindrical shape between the X-ray tube and the X-ray detector.

The control unit 27 includes a CPU (Central Processing Unit) and memory (neither of which is shown). The control unit 27 temporarily stores, in the memory (not shown), information such as an operator instruction, imaging conditions, and fluoroscopy conditions sent from the input unit 23.

The control unit 27 controls the X-ray tube 3, the support frame driving device 9, CT gantry 28, and the like to execute X-ray imaging according to the operator instruction, imaging conditions, and the like stored in the memory. The control unit 27 controls the X-ray generation unit 3, the support frame driving device 9, the top plate driving unit, and the like to execute X-ray fluoroscopy according to the operator instruction, fluoroscopy conditions, and the like stored in the memory. The control unit 27 controls the long-axis direction moving mechanism to move the CT gantry 28 to the moving position coordinate. Note that the control unit 27 may control the top plate driving unit to arrange the CT gantry 28 immediately on the moving position coordinate.

(Gantry Moving Position Determination Function)

A gantry moving position determination function is a function of determining the moving position based on the second designation position. The processing (to be referred to as gantry moving position determination processing hereinafter) of the gantry moving position determination function will be described below.

Figure 17:
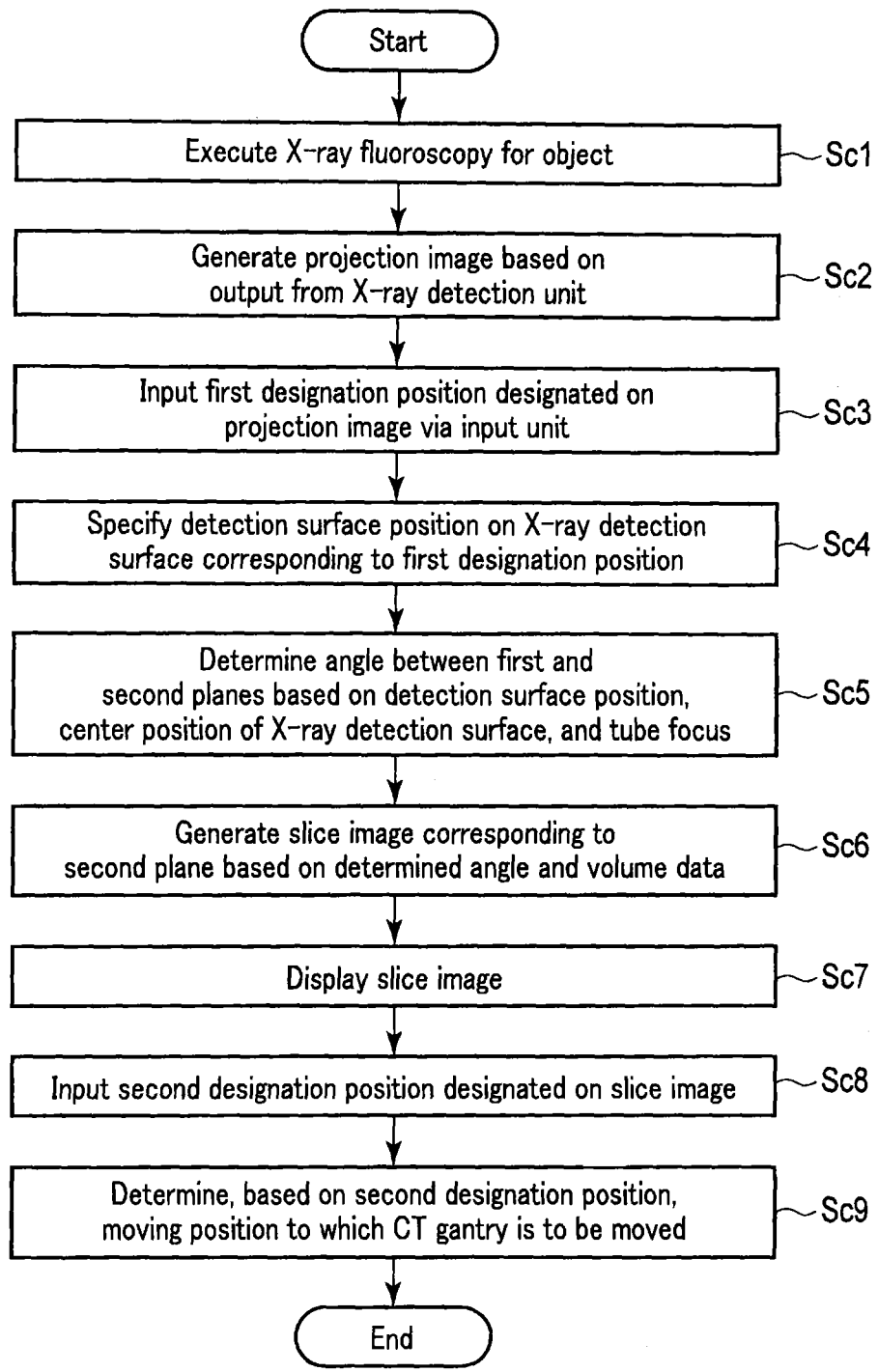
FIG. 17 is a flowchart illustrating an example of the procedure of moving position determination processing according to the second embodiment.

FIG. 17 is a flowchart illustrating an example of the procedure of the gantry moving position determination processing.

X-ray imaging (or fluoroscopy) is executed for the object placed on the top plate 11 (step Sc1). A projection image of the object is generated based on an output from the X-ray detection unit 5 (step Sc2). The first designation position designated on the projection image is input via the input unit 23 (step Sc3). A detection surface position on the X-ray detection surface corresponding to the first designation position is specified (step Sc4). The angle between the first and second planes is determined based on the detection surface position, center position, and tube focus (step Sc5). A slice image corresponding to the second plane is generated based on the determined angle and the volume data (step Sc6). The generated slice image is displayed on the display 25 (step Sc7).

The second designation position designated on the slice image is input (step Sc8). Based on the second designation position, a moving position to which the CT gantry 28 is to be moved is determined (step Sc9). The CT gantry 28 is moved to the determined moving position.

Modification

The difference from the second embodiment is that the moving position determined based on a predetermined height from the top plate 11 and a specific position is corrected based on the second designation position designated on the slice image.

The storage unit 17 stores the predetermined height from the top plate 11 along the Z direction.

The position determination unit 26 determines the first coordinate along the Y-axis based on the specific position and the predetermined height. The position determination unit 26 determines the second coordinate along the Y-axis based on the second designation position. By using the second coordinate, the position determination unit 26 calculates a correction value used to correct the first coordinate. The correction value is, for example, the difference value between the first and second coordinates. The position determination unit 26 determines a moving position based on the first coordinate and the correction value.

Figure 18:
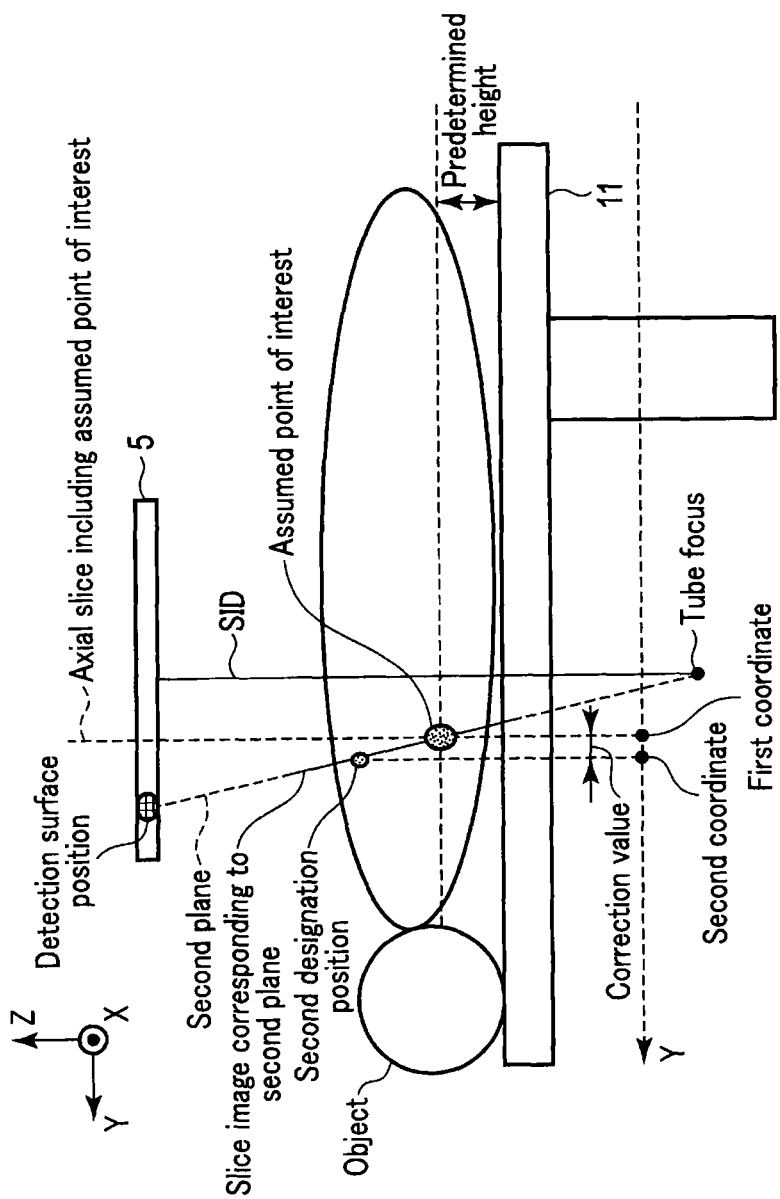
FIG. 18 is a view for explaining an example of a moving position according to a modification of the second embodiment.

The position determination unit 26 outputs a moving position coordinate corresponding to the determined moving position to the CT gantry 28. FIG. 18 is a view for explaining an example of the moving position. As shown in FIG. 18, a moving position coordinate is determined based on the difference value (correction value) between the first and second coordinates. The CT gantry 28 (to be described later) is moved to the moving position coordinate.

(Gantry Moving Position Determination Function)

A gantry moving position determination function according to the modification can correct the moving position based on the first coordinate and the difference value between the first and second coordinates.

Figure 19:
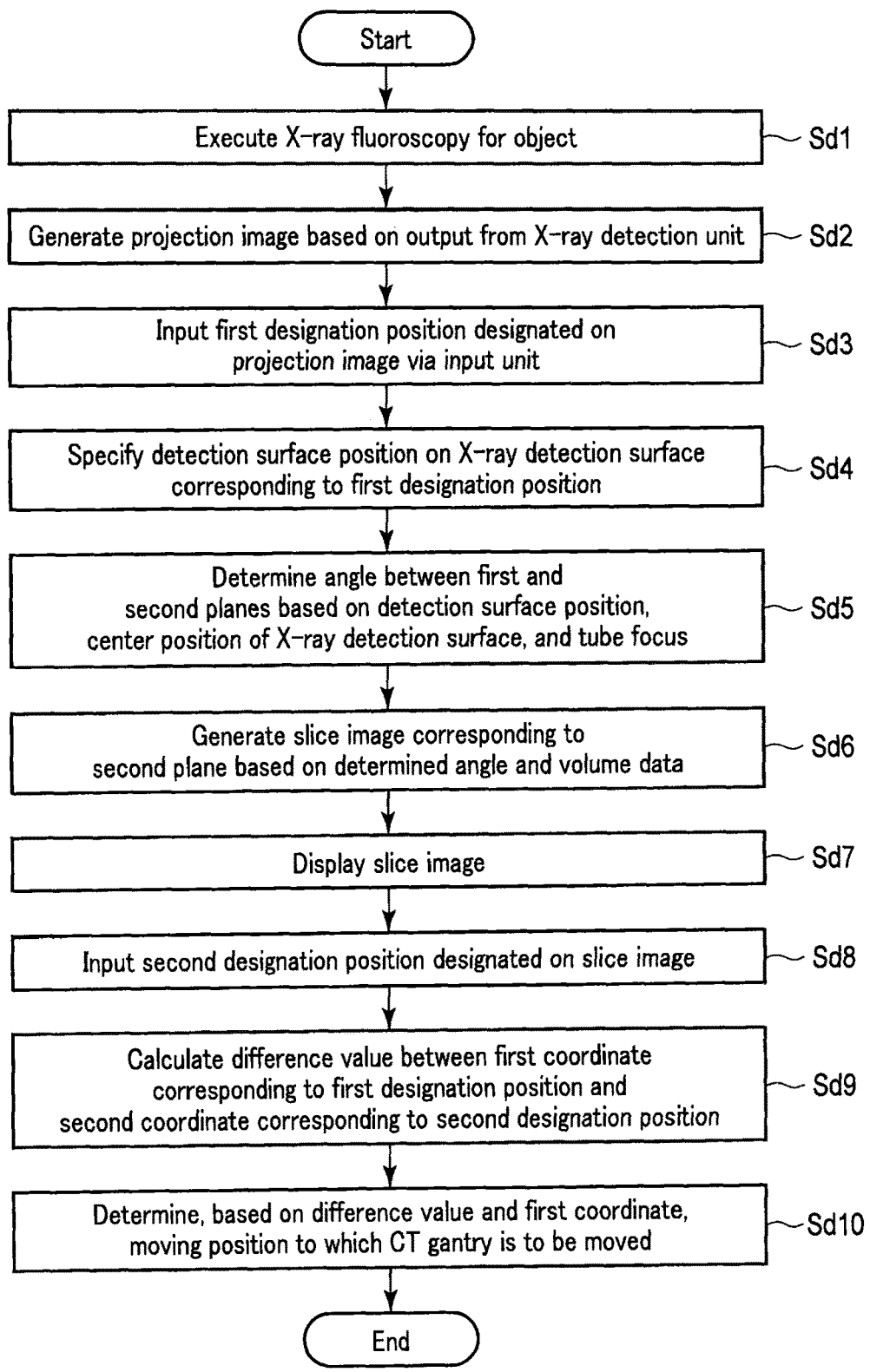
FIG. 19 is a flowchart illustrating an example of the procedure of moving position determination processing according to the modification of the second embodiment.
Figure 20:
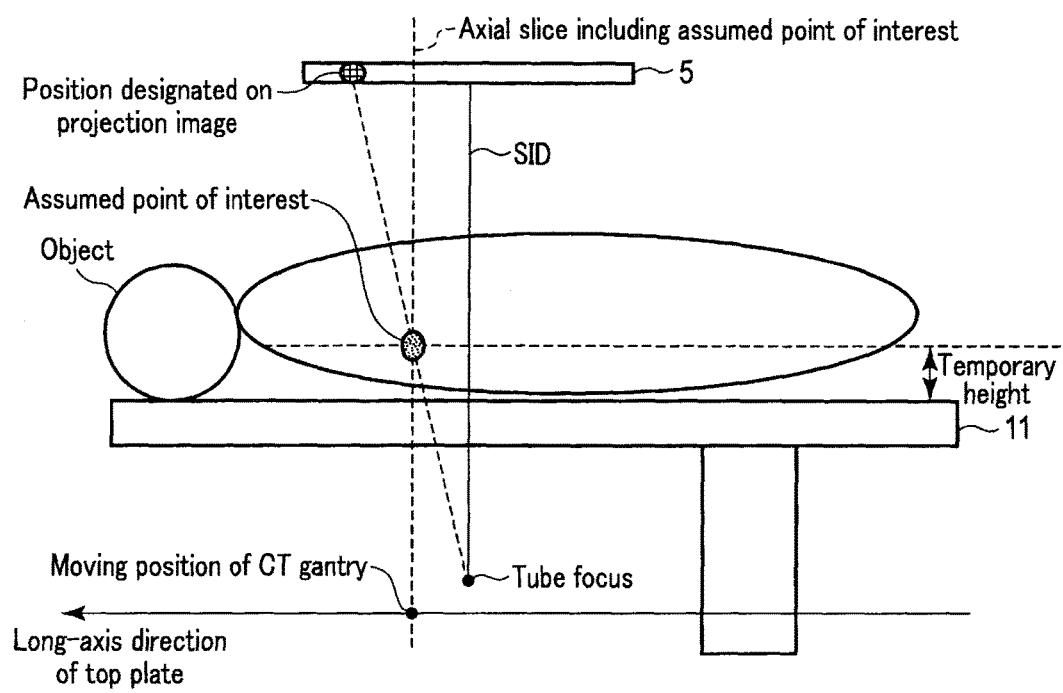
FIG. 20 is a view showing a conventional technique.
Figure 21:
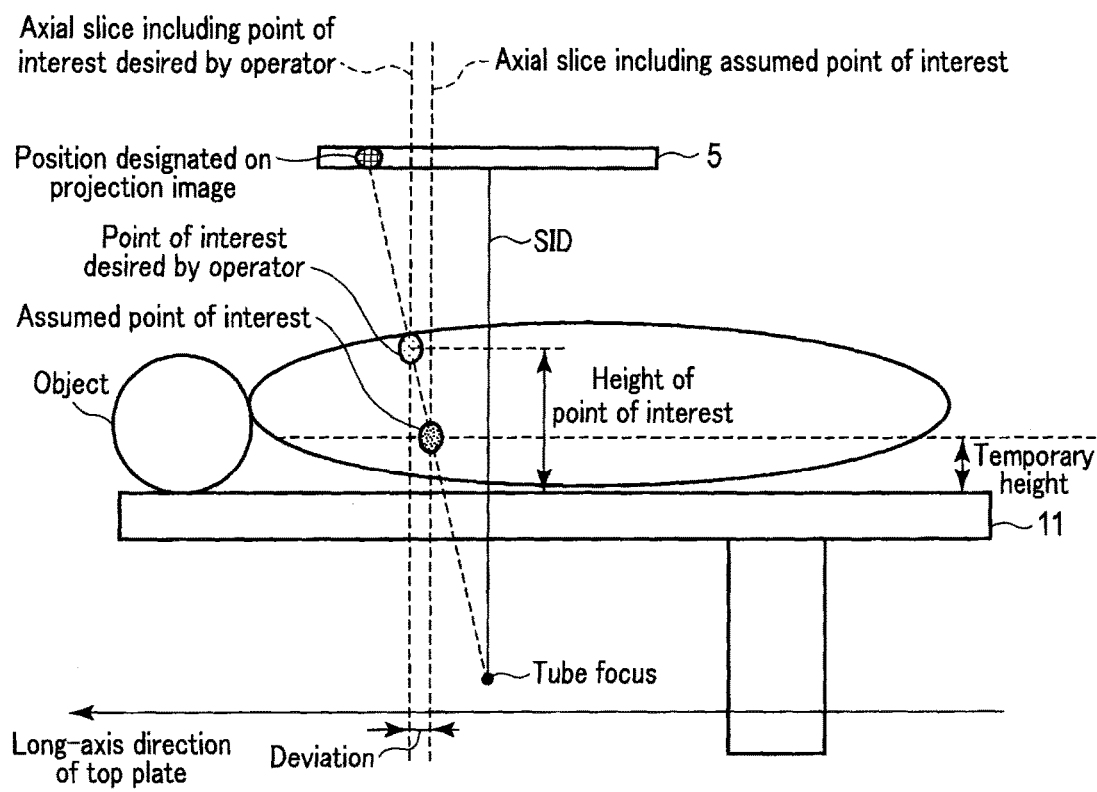
FIG. 21 is a view showing the conventional technique.

FIG. 19 is a flowchart illustrating an example of the procedure of gantry moving position determination processing according to the modification.

X-ray imaging (or fluoroscopy) is executed for the object placed on the top plate 11 (step Sd1). A projection image of the object is generated based on an output from the X-ray detection unit 5 (step Sd2). The first designation position designated on the projection image is input via the input unit 23 (step Sd3). A detection surface position on the X-ray detection surface corresponding to the first designation position is specified (step Sd4). The angle between the first and second planes is determined based on the detection surface position, center position, and tube focus (step Sd5). A slice image corresponding to the second plane is generated based on the determined angle and the volume data (step Sd6). The generated slice image is displayed on the display 25 (step Sd7).

The second designation position designated on the slice image is input (step Sd8). The difference value between the first coordinate corresponding to the first designation position and the second coordinate corresponding to the second designation position is calculated (step Sd9). Based on the first coordinate and difference value, a moving position to which the CT gantry 28 is to be moved is determined (step Sd10). The CT gantry 28 is moved to the determined moving position.

With the above-described arrangement, it is possible to obtain the following effects.

The medical image diagnostic apparatus 1 according to the second embodiment can determine the angle between the first and second planes based on the volume data and the first designation position designated on the projection image, and generate a slice image corresponding to the second plane based on the volume data and the determined angle. Then, the moving position of the CT gantry 28 is determined based on the second designation position designated on the slice image. This can move the CT gantry 28 to a moving position desired by the operator.

As described above, the medical image diagnostic apparatus 1 can determine a moving position desired by the operator with higher accuracy by inputting the second designation position on the slice image generated based on the first designation position designated on the projection image. Also, the medical image diagnostic apparatus 1 need not perform X-ray imaging again, and can thus determine a moving position while decreasing the radiation exposure dose of the object.

According to the modification of the second embodiment, it is possible to determine a moving position by correcting the first coordinate based on the difference value between the first coordinate determined based on the first designation position and the predetermined height and the second coordinate determined based on the second designation position. This can determine a moving position desired by the operator with higher accuracy. Furthermore, the medical image diagnostic apparatus 1 can modify the moving position without executing X-ray imaging again, and move the CT gantry 28 to the modified moving position.

Note that in the modification of the second embodiment, when the technical concept of the medical image diagnostic apparatus 1 is implemented by a medical image processing apparatus, for example, the components surrounded by dotted lines 2 in the view shown in FIG. 10 are included. The respective processes of the gantry moving position determination function according to the second embodiment are, for example, the processes in steps Sc3 to Sc9 in FIG. 17. In addition, the respective processes of the gantry moving position determination function according to the modification of the second embodiment are, for example, the processes in steps Sd3 to Sd10 in FIG. 19.

The function according to the second embodiment can be implemented by installing a program for executing gantry moving position determination processing in a computer such as a work station, and loading it onto a memory. In this case, it is possible to store the program capable of causing the computer to execute the method in a storage medium such as a magnetic disk (Floppy® disk, hard disk, or the like), an optical disk (CD-ROM, DVD, or the like), or a semiconductor memory, and distribute it.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:
1. A medical image diagnostic apparatus comprising:
an X ray tube configured to generate X rays from a predetermined focus;
an X ray detector configured to detect X rays which have been generated by the X ray tube and passed through an object placed on a top plate;
storage circuitry configured to store volume data about the object;
slice image generation circuitry configured to generate a plurality of slice images corresponding to a plurality of planes each including the focus based on the volume data and a relative position of the focus with respect to the top plate;
a display configured to display the slice images;
projection image generation circuitry configured to generate a projection image of the object based on an output from the X ray detector; and
angle determination circuitry configured to determine an angle, based on a position on an X ray detection surface of the X ray detector corresponding to a position designated on the projection image, the position of the focus, and a center position of the X ray detection surface, the angle being between a first plane which includes the position of the focus and the center position and is parallel to a short axis direction of the top plate and a second plane which includes the position of the focus and the position on the X ray detection surface and is parallel to the short axis direction,
wherein the slice image generation circuitry is configured to generate a slice image corresponding to the second plane based on the volume data and the angle.

2. The medical image diagnostic apparatus according to claim 1, wherein the slice image generation circuitry is configured to generate the plurality of slice images at a predetermined interval along a long axis direction of the top plate.

3. The medical image diagnostic apparatus according to claim wherein the display is configured to display the plurality of slice images in an order along the long axis direction.

4. The medical image diagnostic apparatus according to claim 1, further comprising:
a support frame configured to movably support the X ray tube and the X ray detector,
wherein the angle determination circuitry is configured to determine the angle based on a tilt of the support frame, the position on the X ray detection surface, the position of the focus, and the center position.

5. The medical image diagnostic apparatus according to claim 1, further comprising:
position determination circuitry is configured to determine a moving position to which a gantry configured to execute X ray computed tomography for the object is to be moved, based on a position designated on the slice image.

6. The medical image diagnostic apparatus according to claim 5, wherein the position determination circuitry is configured to determine a first coordinate in the long axis direction of the top plate based on the position designated on the projection image and a predetermined height from the top plate, to determine a second coordinate in the long axis direction based on the position designated on the slice image, and to determine the moving position based on the first coordinate and a difference value between the first coordinate and the second coordinate.

7. The medical image diagnostic apparatus according to claim 1, wherein each of the plurality of planes is parallel to the short axis direction of the top plate.

8. The medical image diagnostic apparatus according to claim 1, further comprising:
input circuitry configured to input a point of interest on the slice image corresponding to the second plane,
wherein the slice image generation circuitry is configured to generate three slice images corresponding to three orthogonal slices each including the point of interest, and
the display is configured to display the three slice images.

9. A medical image processing apparatus comprising:
storage circuitry configured to store a projection image and volume data about an object placed on a top plate;
slice image generation circuitry configured to generate, based on the volume data and a relative position between the top plate and an X ray focus with respect to the projection image, a plurality of slice images corresponding to a plurality of planes each including the focus;
a display configured to display the slice images;
angle determination circuitry configured to determine an angle, based on a position on an X ray detection surface corresponding to a position designated on the projection image, a position of the focus, and a center position of the X ray detection surface, the angle being between a first plane which includes the position of the focus and the center position and is parallel to a short axis direction of the top plate and a second plane which includes the position of the focus and the position on the X ray detection surface and is parallel to the short axis direction,
wherein the slice image generation circuitry is configured to generate a slice image corresponding to the second plane based on the volume data and the angle.

10. The medical image processing apparatus according to claim 9, wherein the slice image generation circuitry is configured to generate the plurality of slice images at a predetermined interval along a long axis direction of the top plate.

11. The medical image processing apparatus according to claim 10, wherein the display is configured to display the plurality of slice images in an order along the long axis direction.

12. The medical image processing apparatus according to claim 9, wherein the angle determination circuitry is configured to determine the angle based on a tilt of a support frame configured to movably support an X ray tube and an X ray detector, the position on the X ray detection surface, the position of the focus, and the center position.

13. The medical image processing apparatus according to claim 9, further comprising:
position determination circuitry is configured to determine a moving position to which a gantry configured to execute X ray computed tomography for the object is to be moved, based on a position designated on the slice image.

14. The medical image processing apparatus according to claim 13, wherein the position determination circuitry is configured to determine a first coordinate in a long axis direction of the top plate based on the position designated on the projection image and a predetermined height from the top plate, to determine a second coordinate in the long axis direction based on a position designated on the slice image, and to determine the moving position based on the first coordinate and a difference value between the first coordinate and the second coordinate.

15. The medical image processing apparatus according to claim 9, wherein each of the plurality of planes is parallel to the short axis direction of the top plate.

16. The medical image processing apparatus according to claim 9, further comprising:
input circuitry configured to input a point of interest on the slice image corresponding to the second plane,
wherein the slice image generation circuitry is configured to generate three slice images corresponding to three orthogonal slices each including the point of interest, and
the display is configured to display the three slice images.

17. A medical image processing method comprising:
storing a projection image and volume data about an object placed on a top plate;
generating, based on the volume data and a relative position between the top plate and an X ray focus with respect to the projection image, a plurality of slice images corresponding to a plurality of planes each including a position of the focus;
displaying the slice images;
determining an angle, based on a position on an X ray detection surface corresponding to a position designated on the projection image, the position of the focus, and a center position of the X ray detection surface, the angle being between a first plane which includes the position of the focus and the center position and is parallel to a short axis direction of the top plate and a second plane which includes the position of the focus and the position on the X ray detection surface and is parallel to the short axis direction, wherein the generating generates a slice image corresponding to the second plane based on the volume data and the angle.

18. A gantry moving position determination method comprising:
storing a projection image and volume data about an object;
determining an angle, based on a position on an X ray detection surface corresponding to a first designation position designated on the projection image, a position of an X ray focus with respect to the projection image, and a center position of the X ray detection surface, the angle being between a first plane which includes the position of the focus and the center position and is parallel to a short axis direction of a top plate and a second plane which includes the position of the focus and the position on the X ray detection surface and is parallel to the short axis direction,
generating a slice image corresponding to the second plane based on the volume data and the angle; and
determining, based on a second designation position designated on the slice image, a moving position to which a gantry configured to execute X ray computed tomography for the object is to be moved.

* * * * *